United States Patent [19]
Engel et al.

[11] Patent Number: 5,962,530
[45] Date of Patent: Oct. 5, 1999

[54] AMINO ACID DERIVATIVES, MEDICAMENTS CONTAINING SAID COMPOUNDS AND METHODS OF PRODUCING THEM

[75] Inventors: Wolfhard Engel; Wolfgang Eberlein; Klaus Rudolf, all of Biberach; Henri Doods, Warthausen; Heike-Andrea Wieland, Biberach; Klaus-Dieter Willim, Hochdorf, all of Germany

[73] Assignee: Dr. Karl Thomae GmbH, Biberach, Germany

[21] Appl. No.: 09/077,629

[22] PCT Filed: Nov. 26, 1996

[86] PCT No.: PCT/EP96/05217

§ 371 Date: May 29, 1998

§ 102(e) Date: May 29, 1998

[87] PCT Pub. No.: WO97/19913

PCT Pub. Date: Jun. 5, 1997

[30] Foreign Application Priority Data

Nov. 30, 1995 [DE] Germany .................... 195 44 685

[51] Int. Cl.[6] ............ A01N 47/28; A01N 37/18; C07C 233/31; C07C 275/18
[52] U.S. Cl. ........... 514/595; 514/616; 564/153; 564/155; 564/157; 564/158; 564/56
[58] Field of Search .................. 514/595, 616; 564/153, 155, 157, 158, 56

[56] References Cited

U.S. PATENT DOCUMENTS 5,616,620  4/1997  Rudolf et al. .................. 514/620
5,807,875  9/1998  Rudolf et al. .................. 514/364

FOREIGN PATENT DOCUMENTS 0 230 037 A1  7/1987  European Pat. Off. .
WO 94/17035  8/1994  WIPO .

OTHER PUBLICATIONS

Tsunematsu, H. et al; Chemical and Pharmaceutical Bulletin, "Beta–Naphthylamides of Guanidinophenyl Amino Acids As Substrates of Aminopeptidases"; (1988) 1205–9.36.3.

Tsunematsu, H.; et al J Biochem, Interactions of Derivatives of Guanidinophenylglycine and Guanidinophenylalanine with Trypsin and Related Enzymes (1980) 1773–1783, 88.

Hatanaka, Y.; Biochimica.et Biophysica Acta, "Interactions of Derivatives of Guanidinophenylalanine and Guanidinophenylglycine with *Streptomyces griseus* trypsin" (1985) 274–279, 832.

*Primary Examiner*—Gary Geist
*Assistant Examiner*—Brian J. Davis
*Attorney, Agent, or Firm*—Robert P. Raymond; Alan R. Stempel; Mary-Ellen M. Devlin

[57] ABSTRACT

The invention relates to new amino acid derivatives of general formula (I)

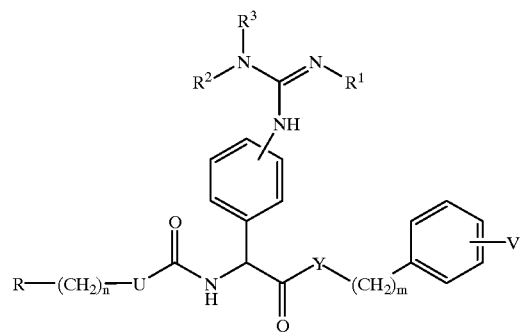

wherein R, U, V, Y, n, m and $R^1$ to $R^3$ are defined as in claim 1, their tautomers, diastereomers, enantiomers, mixtures thereof and salts thereof, particularly the physiologically acceptable salts thereof with inorganic or organic acids or bases, which have valuable pharmacological properties, particularly selective NPY-antagonistic properties, pharmaceutical compositions containing these compounds, the use thereof and processes for preparing them.

8 Claims, No Drawings

AMINO ACID DERIVATIVES, MEDICAMENTS CONTAINING SAID COMPOUNDS AND METHODS OF PRODUCING THEM

The present invention relates to new amino acid derivatives of general formula

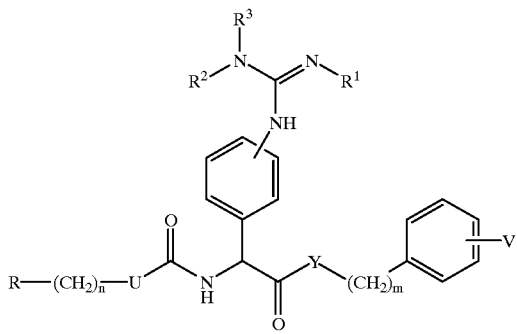

(I)

their tautomers, diastereomers, enantiomers, mixtures thereof and salts thereof, particularly the physiologically acceptable salts thereof with inorganic or organic acids or bases, pharmaceutical compositions containing these compounds, the use thereof and processes for preparing them.

Amino acid derivatives with NPY-antagonistic properties have already been described in WO 94/17035.

In general formula I above

R denotes a phenyl, 1-naphthyl or 2-naphthyl group, a 5-membered heteroaromatic ring linked via a carbon atom and containing a nitrogen, oxygen or sulphur atom or a nitrogen atom and an oxygen, a sulphur or a further nitrogen atom, whilst a nitrogen atom of an imino group may be substituted by an alkyl, alkoxycarbonylalkyl, carboxyalkyl, dialkylaminoalkyl, aminocarbonyl, alkylaminocarbonyl, dialkylaminocarbonyl or alkoxycarbonyl group, or a 6-membered heteroaromatic ring linked via a carbon atom and containing 1, 2 or 3 nitrogen atoms, whilst a 1,4-butadienylene group may be attached both to the 5-membered and to the 6-membered heteroaromatic rings via two adjacent carbon atoms and the bicyclic heteroaromatic rings thus formed may also be bound via a carbon atom of the 1,4-butadienylene group and the groups mentioned for R hereinbefore, including the mono- and bicyclic heteroaromatic rings in their carbon skeleton, may additionally be mono-, di- or at most trisubstituted by fluorine, chlorine or bromine atoms, by alkyl groups, cycloalkyl groups with 3 to 8 carbon atoms, alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano, trifluoromethoxy, trifluoromethylthio, a trifluoromethylsulphynyl or trifluoromethylsulphonyl groups, whilst the substituents may be identical or different and the abovementioned benzoyl, benzoylamino and benzoylmethylamino groups in turn may additionally be substituted in the phenyl moiety by a fluorine, chlorine or bromine atom, an alkyl, trifluoromethyl, amino or acetylamino group, or the diphenylmethyl group, wherein the phenyl groups independently of one another may be mono- or disubstituted by fluorine, chlorine or bromine atoms, methyl, methoxy, hydroxycarbonylmethoxy, alkoxycarbonylmethoxy, hydroxy or trifluoromethyl groups, whilst the substituents in each case may be identical or different, n denotes the numbers 0, 1 or 2, U denotes a single bond, an oxygen atom or the —NH— group, $R^1$ denotes a hydrogen atom, a straight-chained or branched alkyl group with 1 to 8 carbon atoms which may be terminally substituted by a cycloalkyl group with 3 to 8 carbon atoms, or denotes a cycloalkyl group with 3 to 8 carbon atoms, whilst the abovementioned groups may in turn be substituted by an alkoxycarbonyl, phenylalkoxycarbonyl, carboxy, amino, monoalkylamino, dialkylamino or dialkylaminomethyl group, a branched or unbranched alkylcarbonyl group containing 2 to 5 carbon atoms, which may be substituted in the alkyl moiety by an alkoxycarbonyl or phenylalkoxycarbonyl group, by a phenyl group or by a 5- or 6-membered heteroaromatic ring linked via a carbon atom, or a benzoyl group, wherein the phenyl moiety may also be replaced by a 5- or 6-membered heteroaromatic ring linked via a carbon atom, whilst the 5-membered heteroaromatic rings mentioned hereinbefore may contain a nitrogen, an oxygen or a sulphur atom or a nitrogen atom and an additional oxygen, sulphur or further nitrogen atom and may also be substituted by an alkyl group at a nitrogen atom, the 6-membered heteroaromatic rings may contain 1, 2 or 3 nitrogen atoms, and the phenyl groups mentioned hereinbefore may additionally be mono-, di- or at most tri-substituted, as may the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different, the aminocarbonyl group, which may be mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, carboxyalkyl, diphenylalkyl, phenyl, cycloalkyl or cycloalkylalkyl groups with 3 to 8 carbon atoms in the ring in each case, whilst the substituents may be identical or different and the abovementioned phenyl groups may in turn, independently of one another, be mono- or disubstituted by fluorine, chlorine or bromine atoms, methyl, methoxy, hydroxycarbonylmethoxy, alkoxycarbonylmethoxy, hydroxy or trifluoromethyl groups, an alkoxycarbonyl or phenylalkoxycarbonyl group, whilst the phenyl moiety in its turn may be mono- or disubstituted by fluorine, chlorine or bromine atoms, methyl, methoxy, hydroxycarbonylmethoxy, alkoxycarbonylmethoxy, hydroxy or trifluoromethyl groups and the substituents in each case may be identical or different, a phenyl or phenylmethyl group, a hetaryl or hetarylmethyl group linked via a carbon atom, wherein hetaryl denotes a five-membered heteroaromatic ring which contains a nitrogen, oxygen or sulphur atom or a nitrogen atom and an oxygen, sulphur or further nitrogen atom, and wherein a nitrogen atom of an imino group may be substituted by an alkyl group, or a 6-membered heteroaromatic ring linked via a carbon atom, which contains 1, 2 or 3 nitrogen atoms, and wherein the phenyl group may additionally be mono-, di- or at most trisubstituted, as may hetaryl in the carbon skeleton, by fluorine, chlorine or bromine atoms, by alkyl groups, cycloalkyl groups with 3 to 8 carbon atoms, phenylalkyl, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups and the substituents may be identical or different, $R^2$ denotes a hydrogen atom, an alkyl or phenylalkyl group, which may also be mono- or disubstituted in the phenyl moiety by fluorine, chlorine or bromine atoms, alkyl, trifluoromethyl, amino or acetylamino groups, whilst the substituents may be identical or different, $R^3$ denotes a hydrogen atom or an alkyl group, Y denotes an oxygen atom or the —$NR^4$— group wherein $R^4$ denotes a hydrogen atom, a branched or unbranched alkyl group with 1 to 6 carbon atoms or the phenylmethyl group, m denotes the numbers 1 or 2 and V denotes a hydrogen atom, a fluorine, chlorine, bromine or iodine atom, a cyano, alkyl, hydroxy, alkoxy, phenylalkoxy alkylcarbonyl, dialkylamino, hydroxymethyl, hydroxyethyl, hydroxypropyl, hydroxybutyl, trifluoromethyl, trifluoromethoxy or trifluoromethylthio group or the group —$(CH_2)_o$—$Y^1$—W—$Y^2$, wherein o denotes the numbers 0, 1 or 2, W denotes the —$SO_2$— group or the group >C=X wherein X denotes an oxygen atom or one of the divalent groups =N—$CONH_2$ or =N—CN, $Y^1$ denotes a single bond, an oxygen atom or the group —$NR^5$—wherein $R^5$ denotes a hydrogen atom or a straight-chained or branched alkyl group with 1 to 6 carbon atoms or $R^5$ together with the group $Y^2$, the enclosed nitrogen atom and the enclosed group >C=X forms a saturated heterocyclic ring with 5 to 7 ring members, $Y^2$ denotes a straight-chained or branched alkyl group with 1 to 10 carbon atoms optionally substituted by a hydroxy, alkoxycarbonyl or aminocarbonyl group, a cycloalkyl group with 4 to 10 carbon atoms, a straight-chained or branched alkoxy group with 1 to 5 carbon atoms, an aminoalkyl, alkylaminoalkyl, dialkylaminoalkyl, phenylmethoxy or 2-phenylethoxy group, a phenyl or phenylalkyl group with 1 to 3 carbon atoms in the alkyl moiety optionally mono-, di- or trisubstituted in the phenyl moiety by fluorine, chlorine or bromine atoms, by methyl, trifluoromethyl, cyano, amino, hydroxy, methoxy, acetyl, acetylamino, aminocarbonyl, methylaminocarbonyl or dimethylaminocarbonyl groups, or the —$NR^6R^7$ group wherein $R^6$ denotes a hydrogen atom, a straight-chained or branched alkyl group with 1 to 6 carbon atoms optionally substituted by a hydroxy, carboxy, alkoxycarbonyl or dialkylamino group with the proviso that the hydroxy group is not bound in the 1-position of the alkyl group, a cycloalkyl group with 4 to 8 carbon atoms or a phenyl, phenylmethyl, 2-phenylethyl or 3-phenylpropyl group optionally mono-, di- or trisubstituted in the phenyl moiety by fluorine, chlorine or bromine atoms, by methyl, trifluoromethyl, hydroxy, methoxy, amino, acetylamino, aminocarbonyl, methylaminocarbonyl, dimethylaminocarbonyl or cyano groups, whilst the substituents may be identical or different, or an alkanoyl, benzoyl, phenylalkanoyl, alkoxycarbonyl or aminocarbonyl group and $R^7$ has the meanings given for $R^6$ with the exception of a phenyl, alkanoyl, benzoyl, phenylalkanoyl, alkoxycarbonyl or aminocarbonyl group or $R^6$ and $R^7$ together denote an n-alkylene group with 4 to 6 carbon atoms or $R^7$ together with the group $R^5$ of the group —$NR^5$— mentioned for $Y^1$ hereinbefore denotes an unbranched alkylene group or oxoalkylene group with 2 to 4 carbon atoms, whilst all the abovementioned alkyl, cycloalkylalkyl, alkoxy, phenoxycarbonylalkyl, phenylalkoxy, phenylalkoxycarbonyl, phenylalkoxycarbonylalkyl, phenylalkanoyl, phenylalkyl, diphenylalkyl, naphthylalkyl, alkoxycarbonylalkyl, alkoxycarbonylmethoxy, carboxyalkyl, aminoalkyl, monoalkylamino, dialkylamino, alkylaminoalkyl, dialkyl-aminomethyl, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties.

In the definitions given for the groups mentioned hereinbefore:

for example R may denote the phenyl, diphenylmethyl, 2-pyridinyl, 3-pyridinyl, 4-pyridinyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, 1-naphthyl, 2-naphthyl, 1H-indol-2-yl, 1H-indol-3-yl, 1H-indol-4-yl, 1H-indol-5-yl, 1H-indol-6-yl, 1H-indol-7-yl, benzo[b]furan-2-yl, benzo[b]furan-3-yl, benzo[b]thiophen-2-yl, benzo[b]thiophen-3-yl, 2-quinolinyl, 3-quinolinyl, 4-quinolinyl, benzo[c]thiophen-1-yl, 1-isoquinolinyl, 3-isoquinolinyl, 4-isoquinolinyl, pyrazinyl, 2-pyrimidinyl, 4-pyrimidinyl, 5-pyrimidinyl, 3-pyridazinyl, 4-pyridazinyl, 2-imidazolyl, 4-imidazolyl, 1-H-benzimidazol-5-yl, 3-pyrazolyl, 4-pyrazolyl, 1,3-oxazol-2-yl, 1,3-oxazol-4-yl, 1,3-oxazol-5-yl, 3-isoxazolyl, 4-isoxazolyl, 5-isoxazolyl, 2-quinazolinyl, 4-quinazolinyl or 2-quinoxalinyl group, whilst these may additionally be substituted by the groups mentioned hereinbefore, V may denote an acetylaminomethyl, ethoxycarbonylaminomethyl, aminosulphonylaminomethyl, aminocarbonylaminomethyl, aminocarbonylmethyl, methylaminosulphonylmethyl, methoxycarbonylaminomethyl, methylaminocarbonylaminomethyl, benzoylaminomethyl, phenylaminocarbonylaminomethyl, aminosulphonylmethyl, ethylaminocarbonylaminomethyl, 1-methylethylaminocarbonylaminomethyl, [[amino (aminocarbonylimino)methyl]amino]methyl, ethoxycarbonylaminocarbonylaminomethyl, dimethylaminocarbonylaminomethyl, aminocarbonyloxymethyl, tert.butoxycarbonylaminomethyl, aminocarbonylaminocarbonyl-aminomethyl, [(amino (cyanimino)methyl]amino]methyl, methoxycarbonylmethyl, methylaminocarbonylmethyl, [[(dimethylamino)carbonyl]methylamino]methyl, [(aminocarbonyl)methylamino]methyl, [[(methylamino) carbonyl]methylamino]methyl, [(methoxycarbonyl) methylamino]methyl, [[(carboxymethyl)amino]carbonyl] methyl, [[[bis(carboxymethyl)]amino]carbonyl]methyl, [[[bis(methoxycarbonylmethyl)]amino]carbonyl]methyl, [(ethoxycarbonylaminocarbonyl)methylamino]methyl, ethoxycarbonylmethylaminocarbonylaminomethyl, carboxymethylaminocarbonylaminomethyl, dimethylaminocarbonylmethyl, 2-(aminocarbonyl)ethyl, (2-oxo-1-imidazolidinyl)methyl, 2-(3-methyl-1,2,4-oxadiazol-5-yl)ethyl, 2-(methoxycarbonyl)ethyl, [(4-amino-1,4-dioxobutyl)amino]methyl or 2-(aminocarbonylamino)ethyl group and $R^1$ may denote a methyl, methoxycarbonyl, ethoxycarbonyl, propyloxycarbonyl, butyloxycarbonyl, methoxycarbonylethylcarbonyl, aminocarbonyl, methylaminocarbonyl, ethylaminocarbonyl, dimethylaminocarbonyl, propylaminocarbonyl, butylaminocarbonyl, phenylaminocarbonyl, benzylaminocarbonyl, (2-phenylethyl)aminocarbonyl, (3-phenylpropyl)aminocarbonyl, (3,3-diphenylpropyl)aminocarbonyl, 1-naphthylmethylaminocarbonyl, 2-naphthylmethylaminocarbonyl, cyclohexylaminocarbonyl, 4-(4-methoxyphenyl)-butylaminocarbonyl, hydroxycarbonylethylaminocarbonyl, ethoxycarbonylethylaminocarbonyl, methoxyphenyl, 4-(dimethylaminomethyl)cyclohexylmethyl, benzoyl, 4-fluorobenzoyl, nicotinoyl, iso-nicotinoyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, pyrazinyl, 2-pyrimidinyl, 4-pyrimidinyl, 5-pyrimidinyl, 3-pyridazinyl, 4-pyridazinyl, 2-imidazolyl, 4-imidazolyl, 3-pyrazolyl, 4-pyrazolyl, 1,3-oxazol-2-yl, 1,3-oxazol-4-yl, 1,3-oxazol-5-yl, 3-isoxazolyl, 4-isoxazolyl, 5-isoxazolyl, 2-thiazolyl, 4-methyl-2-thiazolyl, 5-methyl-2-thiazolyl, 4-(2-phenylethyl)-2-thiazolyl, 4-(3-phenylpropyl)-2-thiazolyl, 2-pyridinyl, 3-pyridinyl, 4-pyridinyl or 5-methyl-2-pyridinyl group.

The present invention relates to the racemates, if in compounds of general formula I the asymmetric carbon atom of the central amino acid is the only chiral element. However, the application also includes the individual diastereomers or the mixtures thereof which occur when a compound of general formula I contains two or more chiral elements. Particularly preferred are the compounds of general formula I which are in the (D) or (R) configuration with respect to the partial amino acid structure

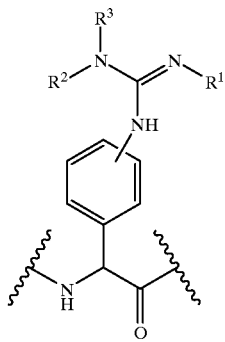

The compounds of general formula I have valuable pharmacological properties, based on their selective NPY-antagonistic properties. The invention further relates to pharmaceutical compositions containing these compounds, their use and the preparation thereof.

Compounds of general formula

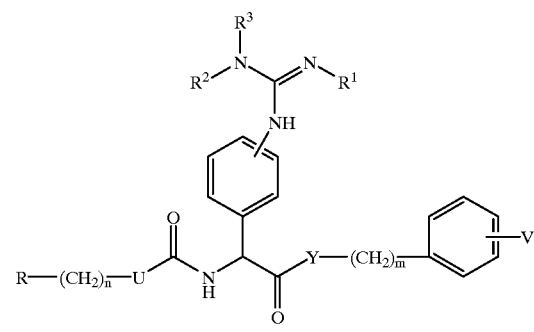

are preferred, wherein

R, n, U, $R^1$, $R^2$, $R^3$, V, Y and m are as hereinbefore defined,

V is bound in the 3- or 4-position of the benzene ring and denotes a hydrogen atom, a fluorine, chlorine, bromine or iodine atom, a cyano, alkyl, hydroxy, alkoxy, alkylcarbonyl, dialkylamino, hydroxymethyl, hydroxyethyl, hydroxypropyl, hydroxybutyl, trifluoromethyl, trifluoromethoxy, trifluoromethylthio group or the group —$(CH_2)_o$—$Y^1$—(CO)—W—$Y^2$ wherein o, $Y^1$ and $Y^2$ are as hereinbefore defined, whilst, unless otherwise specified, the alkyl, alkoxy, alkylcarbonyl and dialkylamino groups mentioned for V hereinbefore may contain 1 to 5 carbon atoms in the alkyl and alkoxy moieties, their tautomers, diastereomers, enantiomers and the salts thereof.

Particularly preferred are those compounds of general formula Ia above wherein

R denotes a phenyl, 1-naphthyl or 2-naphthyl group, a 5-membered heteroaromatic ring linked via a carbon atom, which contains a nitrogen, oxygen or sulphur atom, whilst a nitrogen atom of an imino group may be substituted by an alkyl group, or a 6-membered heteroaromatic ring linked via a carbon atom, which contains 1 or 2 nitrogen atoms, whilst the groups mentioned for R hereinbefore, including the heteroaromatic rings in their carbon skeleton, may additionally be substituted by a fluorine, chlorine or bromine atom, by an alkyl group, by a cycloalkyl group with 3 to 6 carbon atoms, by an alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano or trifluoromethoxy group, or the diphenylmethyl group wherein the phenyl groups may be substituted independently of one another by a fluorine, chlorine or bromine atom, by a methyl, methoxy, hydroxycarbonylmethoxy, alkoxycarbonylmethoxy, hydroxy or trifluoromethyl group, n denotes the number 0 or 1, U denotes a single bond, $R^1$ denotes a hydrogen atom, a straight-chained or branched alkyl group having 1 to 5 carbon atoms which may be terminally substituted by a cycloalkyl group having 4 to 7 carbon atoms, or denotes a cycloalkyl group having 4 to 7 carbon atoms, whilst the abovementioned groups may in turn be substituted by an alkoxycarbonyl, phenylalkoxycarbonyl, carboxy, amino, monoalkylamino, dialkylamino or dialkylaminomethyl group, a branched or unbranched aliphatic acyl group containing 2 to 4 carbon atoms which may be substituted by an alkoxycarbonyl or phenylalkoxycarbonyl group or by a phenyl group optionally substituted by a fluorine, chlorine or bromine atom, by an alkyl group, a cycloalkyl group with 4 to 7 carbon atoms, or by an alkoxy, trifluoromethyl, hydroxy, amino, acetylamino or cyano group, or a benzoyl group, the aminocarbonyl group, which may be substituted at the nitrogen atom by an alkyl, phenylalkyl, (1-naphthyl)alkyl, (2-naphthyl)alkyl, alkoxycarbonylalkyl, carboxyalkyl, ω,ω-diphenylalkyl, phenyl, cycloalkyl or cycloalkylalkyl groups each with 3 to 6 carbon atoms in the ring, whilst the phenyl groups in the abovementioned groups may in turn be substituted by a fluorine, chlorine or bromine atom, or by a methyl, methoxy, hydroxy or trifluoromethyl group, an alkoxycarbonyl or phenylalkoxycarbonyl group, which may be substituted in the phenyl moiety by a fluorine, chlorine or bromine atom, by a methyl, methoxy, hydroxy or trifluoromethyl group, a phenyl group or a five-membered heteroaromatic ring bound via a carbon atom, which contains a nitrogen, oxygen or sulphur atom, whilst a nitrogen atom of an imino group may be substituted by an alkyl group, or a 6-membered heteroaromatic ring linked via a carbon atom, which contains 1 or 2 nitrogen atoms, whilst the phenyl group may additionally be substituted, as may the 5- and 6-membered heteroaromatic rings in their carbon skeleton, by a fluorine, chlorine or bromine atom, by an alkyl group, by a cycloalkyl group with 3 to 6 carbon atoms, by a phenylalkyl, alkoxy, trifluoromethyl, hydroxy or amino group, $R^2$ denotes a hydrogen atom, an alkyl group or a phenylalkyl group optionally substituted in the phenyl moiety by a fluorine, chlorine or bromine atom or by an alkyl, trifluoromethyl, amino or acetylamino group, $R^3$ denotes a hydrogen atom or the methyl group, Y denotes an oxygen atom or the —$NR^4$— group wherein $R^4$ denotes a hydrogen atom, the methyl or ethyl group, m denotes the number 1 and V, which is bound in the 4 position of the benzene ring, denotes a hydrogen, fluorine, chlorine or bromine atom, a cyano, alkyl, hydroxy, alkoxy, phenylalkoxy, alkylcarbonyl, dialkylamino, hydroxymethyl, hydroxyethyl, hydroxypropyl, hydroxybutyl or trifluoromethyl group or the group —$(CH_2)_o$—$Y^1$—$(CO)$—$Y^2$ wherein o denotes the number 0 or 1, $Y^1$ denotes a single bond, an oxygen atom or the group —$NR^5$, wherein $R^5$ denotes a hydrogen atom or a straight-chained or branched alkyl group with 1 to 4 carbon atoms or $R^5$ together with the group $Y^2$, the enclosed nitrogen atom and the enclosed group >C=O forms a saturated heterocyclic ring with 5 to 7 ring members, and $Y^2$ denotes a straight-chained or branched alkyl group with 1 to 5 carbon atoms optionally substituted by a hydroxy, alkoxycarbonyl or aminocarbonyl group, an alkoxy group with 1 to 3 carbon atoms, an aminoalkyl, alkylaminoalkyl or dialkylaminoalkyl group or a phenyl or phenylalkyl group with 1 to 3 carbon atoms in the alkyl moiety optionally substituted in the phenyl moiety by a fluorine, chlorine or bromine atom, by a methyl, trifluoromethyl, cyano, amino, hydroxy or methoxy group or the —$NR^6R^7$ group wherein $R^6$ denotes a hydrogen atom, a straight-chained or branched alkyl group with 1 to 6 carbon atoms, a cycloalkyl group with 4 to 6 carbon atoms or a phenyl group optionally substituted by a fluorine, chlorine or bromine atom, by a methyl, trifluoromethyl, hydroxy or methoxy group, and $R^7$ has the meanings given for $R^6$ with the exception of a phenyl group, whilst all the abovementioned alkyl, alkoxy, phenylalkyl, ω,ω-diphenylalkyl, naphthylalkyl, cycloalkylalkyl, phenylalkoxy, phenylalkoxycarbonyl, alkoxycarbonylalkyl, alkoxy-carbonylmethoxy, carboxyalkyl, alkylamino, dialkylamino, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties, their tautomers, diastereomers, enantiomers and the salts thereof.

Most particularly preferred are the compounds of general formula Ia above wherein R denotes a diphenylmethyl group wherein the phenyl groups independently of one another may be substituted by a methyl group, n denotes the number 0, U denotes a single bond, $R^1$ denotes a hydrogen atom, a straight-chained or branched alkyl group with 1 to 3 carbon atoms which may be terminally substituted by a cycloalkyl group with 4 to 6 carbon atoms, whilst the cycloalkyl group may in turn be substituted by a dialkylaminomethyl group with 1 to 3 carbon atoms in the alkyl moieties, the aminocarbonyl group, which may be substituted at the nitrogen atom by an alkyl group with 1 to 3 carbon atoms, or a phenyl group optionally substituted by an alkyl or alkoxy group with 1 to 3 carbon atoms, $R^2$ denotes a hydrogen atom or an alkyl group with 1 to 3 carbon atoms optionally substituted by a phenyl group, $R^3$ denotes a hydrogen atom or the methyl group, Y denotes the —$NR^4$ group wherein $R^4$ denotes a hydrogen atom, the methyl or ethyl group, m denotes the number 1 and V, which is bound in the 4 position of the benzene ring, denotes a hydrogen atom, a hydroxy or phenylalkoxy group with 1 to 3 carbon atoms in the alkoxy moiety or the group —$(CH_2)_o$—$Y^1$—$(CO)$—$Y^2$ wherein $Y^1$ denotes a single bond or the group —$NR^5$, wherein $R^5$ denotes a hydrogen atom or a straight-chained or branched alkyl group with 1 to 3 carbon atoms, and $Y^2$ denotes the —$NR^6R^7$ group wherein $R^6$ and $R^7$ independently of one another denote a hydrogen atom or a straight-chained or branched alkyl group having 1 to 3 carbon atoms, their tautomers, diastereomers, enantiomers and the salts thereof.

The following are mentioned as examples of particularly preferred compounds:

(1) (R,S)-3-(Aminoiminomethylamino)-α-[(diphenylacetyl)amino]-N-[(4-hydroxyphenyl) methyl]-benzeneacetamide, (2) (R,S)-N-[[4-(Aminocarbonylaminomethyl)phenyl] methyl]-3-(aminoiminomethylamino)-α-[(diphenylacetyl)amino]-benzeneacetamide, (3) (R,S)-N-[[4-(Aminocarbonylmethyl)phenyl]methyl]-3-(aminoiminomethylamino)-α-[(diphenylacetyl) amino]-benzeneacetamide, (4) trans-(R,S)-3-[[4-(Dimethylaminomethyl) cyclohexylmethyl]-aminoiminomethylamino]-α-

[(diphenylacetyl)amino]-N-methyl-N-(phenylmethyl)-benzeneacetamide, (5) (R,S)-α-[(Diphenylacetyl)amino]-N-methyl-3-(phenylaminoiminomethylamino)-N-(phenylmethyl)benzeneacetamide, (6) (R,S)-3-(Aminoiminomethylamino)-α-[(diphenylacetyl)amino]-N-methyl-N-(phenylmethyl)-benzeneacetamide, (7) (R,S)-α-[(Diphenylacetyl)amino]-N-methyl-3-(methylaminoiminomethylamino)-N-(phenylmethyl)benzeneacetamide, (8) trans-(R,S)-N-[[4-(Aminocarbonylaminomethyl)phenyl]methyl]-3-[[4-(dimethylaminomethyl)cyclohexylmethyl]aminoiminomethylamino]-α-[(diphenylacetyl)amino]-benzeneacetamide, (9) (R,S)-N-[[4-(Aminocarbonylaminomethyl)phenyl]methyl]α-[(diphenylacetyl)amino]-3-[(methylaminocarbonyl)aminoiminomethylamino]-benzeneacetamide,

(10) (R,S)-N-[[4-(Aminocarbonylaminomethyl)phenyl]methyl]α-[(diphenylacetyl)amino]-3-[(4-methoxyphenyl)aminoiminomethylamino]-benzeneacetamide,

(11) (R,S)-α-[(Diphenylacetyl)amino]-3-[(4-methoxyphenyl)aminoiminomethylamino]-N-(phenylmethyl)benzeneacetamide,

(12) (R,S)-N-[[4-(Aminocarbonylaminomethyl)phenyl]methyl]-α-[(diphenylacetyl)amino]-3-[[imino[N-methyl-N-(phenylmethyl)amino]methyl]amino]-benzeneacetamide,

(13) (R,S)-N-[[4-(Aminocarbonylaminomethyl)phenyl]methyl]-α-[(diphenylacetyl)amino]-3-(methylaminoiminomethylamino)-benzeneacetamide,

(14) (R,S)-α-[(Diphenylacetyl)amino]-3-[(4-methoxyphenyl)aminoiminomethylamino]-N-[[(4-phenylmethoxy)phenyl]methyl]-benzeneacetamide,

(15) (R,S)-3-(Aminoiminomethylamino)-α-[(diphenylacetyl)amino]-N-[[(4-phenylmethoxy)phenyl]methyl]-benzeneacetamide,

(16) (R,S)-3-(Aminoiminomethylamino)-α-[(diphenylacetyl)amino]-N-methyl-N-[[(4-phenylmethoxy)phenyl]methyl]benzeneacetamide,

(17) (R,S)-N-[[4-(Aminocarbonylaminomethyl)phenyl]methyl]-α-[(diphenylacetyl)amino]-N-methyl-3-(methylaminoiminomethylamino)-benzeneacetamide and the salts thereof.

The compounds of general formula I are prepared by methods known in principle, whilst processes derived from peptide chemistry (cf for example Houben-Weyl, Methoden der Organischen Chemie, vol. 15/2) may particularly be used. The amino protecting groups used may be those described in Houben-Weyl, Methoden der Organischen Chemie, vol. 15/1, whilst urethane protecting groups, such as, for example, the fluorenylmethoxycarbonyl, phenylmethoxycarbonyl or tert.-butyloxycarbonyl group, are preferred. Any functional groups present in the precursors for synthesising the compounds of general formula I, such as guanidino or amino functions, may be protected by suitable protecting groups to prevent side reactions (cf for example: G. B. Fields et al., Int. J. Peptide Protein Res. 35, 161 (1990); T. W. Greene, Protective Groups in Organic Synthesis). Care should be taken in particular to ensure that so-called orthogonal combinations of protecting groups are used for protecting the α-amino and the side chain function, e.g.:

| Protection of the N (side chain) | N$^\alpha$-protection |
|---|---|
| p-toluenesulphonyl | phenylmethoxycarbonyl<br>tert.butyloxycarbonyl |
| phenylmethoxycarbonyl | (4-methoxyphenyl)methoxycarbonyl<br>tert. butoxycarbonyl<br>adamantyloxycarbonyl<br>biphenylylisopropyloxycarbonyl<br>isonicotinoyloxycarbonyl<br>o-nitrophenylsulphenyl<br>formyl |
| tert. butoxycarbonyl | phenylmethoxycarbonyl<br>p-toluenesulphonyl<br>o-nitrophenylsulphenyl<br>biphenylylisopropyloxycarbonyl<br>9-fluorenylmethoxycarbonyl |
| acetyl, trifluoroacetyl, formyl, (2-chlorophenyl)-methoxycarbonyl, (4-chlorophenyl)methoxycarbonyl, 4-(nitrophenyl)methoxycarbonyl, phthaloyl | tert.butyloxycarbonyl |

Instead of protecting amino groups in the side chain, it is also possible to use phenylglycine which carries precursor functions and is substituted in the side chain, particularly by nitro, or the derivatives thereof, such as α-amino-3-nitrobenzeneacetic acid.

The basic functions in the side chain of commercially unobtainable amino acids which are characterised, for example, by (aminoiminomethylamino) groups may be protected by the same method as is used for protecting the side chain of arginine and its derivatives (cf. also M. Bodanszky, "Peptide Chemistry", Springer-Verlag, 1988, pp. 94–97); protecting groups which are particularly suitable for the (aminoiminomethylamino) group include the p-toluenesulphonyl, mesitylenesulphonyl (Mts), methoxytrimethylphenylsulphonyl (Mtr), 2,2,5,7,8-pentamethylchromane-6-sulphonyl (Pmc), pentachlorophenoxycarbonyl and nitro protecting groups.

For the actual coupling the methods known from peptide chemistry (cf for example Houben-Weyl, Methoden der Organischen Chemie, vol. 15/2) are used. Preferably, carbodiimides, such as e.g. dicyclohexylcarbodiimide (DCC), diisopropylcarbodiimide (DIC) or ethyl-(3-dimethylaminopropyl)-carbodiimide, O-(1H-benzotriazol-1-yl)-N,N,N',N'-tetramethyluroniumhexafluorophosphate (HBTU) or -tetrafluoroborate (TBTU) or 1H-benzotriazol-1-yl-oxy-tris-(dimethylamino) phosphoniumhexafluorophosphate (BOP), are used. If desired, it is also possible to suppress racemisation or speed up the reaction by the addition of 1-hydroxybenzotriazole (HOBt) or 3-hydroxy-4-oxo-3,4-dihydro-1,2,3-benzotriazine (HOObt). The couplings are normally carried out with equimolar amounts of the coupling components and the coupling reagent in solvents such as dichloromethane, tetrahydrofuran, acetonitrile, dimethylformamide (DMF), dimethylacetamide (DMA), N-methylpyrrolidone (NMP) or mixtures thereof and at temperatures of between −30 and +30° C., preferably −20 and +20° C. If necessary, N-ethyl-diisopropylamine (DIEA; Hünig base) is preferred as an additional auxiliary base.

The so-called "anhydride method" (cf. also: M. Bodanszky, "Peptide Chemistry", Springer-Verlag 1988, P. 58–59; M. Bodanszky, "Principles of Peptide Synthesis", Springer-Verlag 1984, P. 21–27) is used as another coupling method for synthesising compounds of general formula I. It is preferable to use the "mixed anhydride method" in the variant according to Vaughan (J. R. Vaughan Jr., J. Amer.

Chem. Soc. 73, 3547 (1951)), in which the mixed anhydride is obtained from the optionally $N^2$-protected α-amino acid and the monoisobutyl carbonate which are to be coupled, using isobutyl chlorocarbonate in the presence of bases such as 4-methylmorpholine or 4-ethylmorpholine. The preparation of this mixed anhydride and the coupling with amines are carried out in a one-pot method, using the abovementioned solvents and at temperatures between −20 and +20° C., preferably 0 and +20° C.

Any protecting groups present in the α-amino acid side chain are finally cleaved after the synthesis of the N- and C-terminally substituted amino acid derivative with suitable reagents which are also in principle known from the literature, namely arylsulphonyl and hetarylsulphonyl protecting groups are preferably cleaved acidolytically, i.e. by the action of strong acids, preferably trifluoroacetic acid, nitro and arylmethoxycarbonyl protecting groups are cleaved hydrogenolytically, e.g. with hydrogen in the presence of palladium black and using glacial acetic acid as solvent. If the substrate contains functions which are sensitive to hydrogenolysis, e.g. halogen atoms, such as chlorine, bromine or iodine, a phenylmethanol or hetarylmethanol function or another benzylheteroatom bond, particularly a benzyl-oxygen bond, the cleaving of the nitro group may also be carried out non-hydrogenolytically, e.g. with zinc/2N trifluoroacetic acid (cf also: A. Turan, A. Patthy and S. Bajusz, Acta Chim. Acad. Sci. Hung., Tom. 85 (3), 327–332 [1975]; C. A. 83, 206526y [1975]), with tin(II)chloride in 60% aqueous formic acid (cf also: SUNSTAR KK, JA-A-3271-299), with zinc in the presence of acetic acid (cf also: A. Malabarba, P. Ferrari, G. Cietto, R. Pallanza and M. Berti, J. Antibiot. 42 (12)1800–1816 (1989)) or excess aqueous 20% titanium(III)chloride in aqueous methanol and in the presence of aqueous ammonium acetate buffer at 24° C. (cf also: R. M. Freidinger, R. Hirschmann and D. F. Veber, J. Org. Chem. 43 (25), 4800–4803 [1978]).

The following processes are particularly suitable for preparing the compounds of general formula I according to the invention:

a) Coupling compounds of general formula II,

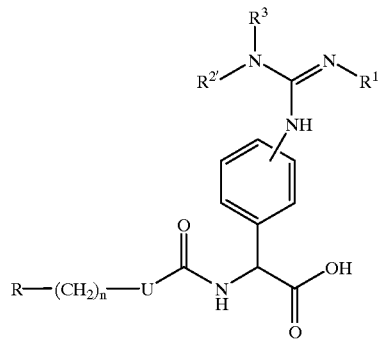

wherein

R, $R^1$, $R^3$, U and n are as hereinbefore defined and $R^{2'}$ has the meanings given for $R^2$ hereinbefore or also denotes one of the protecting groups mentioned hereinbefore for the protection of side chains carrying guanidino functions,
with compounds of general formula III,

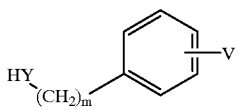

wherein m, V and Y have the meanings given hereinbefore, and, if necessary, subsequently cleaving protecting groups using the methods described hereinbefore.

The coupling is carried out using the methods known from peptide chemistry and described hereinbefore, particularly using DCC, DIC, HBTU, TBTU or BOP as reagents or using the mixed anhydride method.

If the starting compound II used is enantiomerically pure, then, if U does not represent an oxygen atom or an NH group, partial racemisation must be expected during the coupling step if triethylamine is used as the auxiliary base and dimethylformamide, dimethylacetamide or N-methylpyrrolidone is used as solvent and in some cases substantial or even quantitative racemisation must be expected.

For preparing compounds of general formula I wherein Y denotes an oxygen atom, the variant recommended by A. Hassner and V. Alexonian, Tetrahedron Letters 1978, 4475–4478, i.e. reaction at ambient temperature and in the presence of DCC and 4-(1-pyrrolidinyl)pyridine as base, has proved particularly successful.

b) For preparing compounds of general formula I wherein U has the meanings given hereinbefore with the exception of an oxygen atom and the —NH— group:

Coupling compounds of general formula IV,

$$R\text{---}(CH_2)_n\text{---}CO\text{---}Nu \qquad (IV)$$

wherein

R and n are as hereinbefore defined and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, by methyl or nitro groups, whilst the substituents may be identical or different, with α-amino acid derivatives of general formula V,

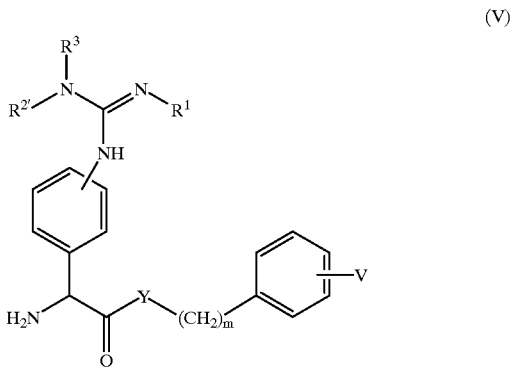

wherein $R^1$, $R^3$, V, Y and m are as hereinbefore defined and $R^{2'}$ has the meanings given for $R^2$ hereinbefore or also denotes one of the protecting groups mentioned hereinbefore for protecting the side chains carrying guanidino functions, and, if necessary, subsequently cleaving protecting groups using the methods described hereinbefore.

If in general formula IV Nu denotes the hydroxy group, the coupling methods known from peptide chemistry and discussed in detail above will be used, particularly using the abovementioned coupling reagents DCC, DIC, HBTU, TBTU or BOP, or the mixed anhydride method will be used.

If in general formula IV Nu denotes a halogen atom, an alkyl or arylsulphonyloxy group, the reaction is carried out under Schotten-Baumann or Einhorn conditions, i.e. the components are reacted in the presence of at least one equivalent of an auxiliary base at temperatures of between $-50°$ C. and $+120°$ C., preferably $-10°$ C. and $+30°$ C., and optionally in the presence of solvents. Examples of preferred auxiliary bases include alkali and alkaline earth hydroxides, for example sodium hydroxide, potassium hydroxide or barium hydroxide, alkali metal carbonates, e.g. sodium carbonate, potassium carbonate or caesium carbonate, alkali metal acetates, e.g. sodium or potassium acetate, and tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, preferred solvents include for example dichloromethane, tetrahydrofuran, 1,4-dioxan, acetonitrile, dimethylformamide, dimethylacetamide, N-methyl-pyrrolidone or mixtures thereof; if alkali or alkaline earth hydroxides, alkali metal carbonates or acetates are used as auxiliary bases, water may also be added to the reaction mixture as a cosolvent.

c) For preparing compounds of general formula I wherein Y denotes an oxygen atom:

Transesterifying amino acid esters of general formula VI,

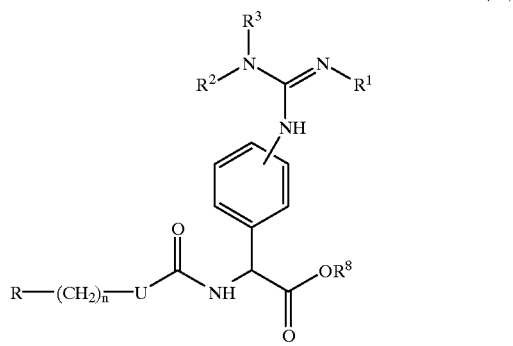

(VI)

wherein $R, R^1, R^2, R^3, U$ and n are as hereinbefore defined and $R^8$ denotes an alkyl group with 1 to 4 carbon atoms, with an alcohol of general formula VII,

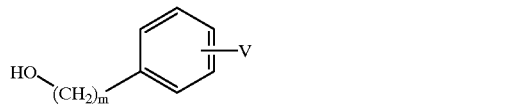

(VII)

wherein m and V are as hereinbefore defined.

The transesterification may be catalysed with an acid or alkaline catalyst (cf. also: J. March, "Advanced Organic Chemistry", John Wiley.& Sons, Third Edition, 1985, P. 351–352). Preferred alkaline catalysts are the corresponding alkali metal alkoxides which are easily obtained from the alcohols of general formulae VII or $R^8OH$, e.g. lithium, sodium or potassium alkoxides; preferred acid catalysts include, in addition to anhydrous hydrogen chloride, in particular, sulphuric acid, p-toluene-sulphonic acid, naphthalene-1- or -2-sulphonic acid or acid ion exchanger freshly charged with hydrogen ions, e.g. Wofatit KPS z.A. The equilibrium between the two esters in the equation is shifted in the right direction in this process by distilling off the more volatile alcohol $R^8OH$.

With alkaline catalysis, if the starting compound VI used was enantiomerically pure, the end product of general formula I is obtained as a racemate.

d) For preparing compounds of general formula I wherein Y denotes an oxygen atom:

Reacting salts, preferably alkali metal salts, of the carboxylic acids of general formula II,

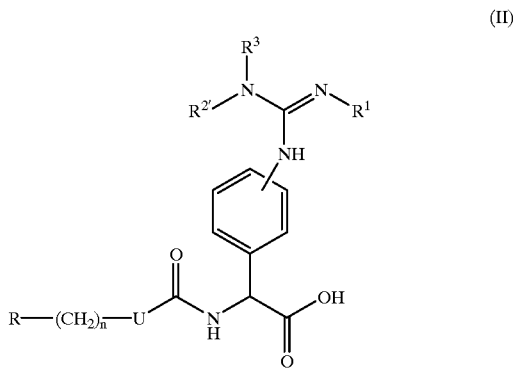

(II)

wherein $R, R^1, R^3, U$ and n are as hereinbefore defined and $R^{2'}$ has the meanings given for $R^2$ hereinbefore or also denotes one of the protecting groups mentioned hereinbefore for protecting the side chains carrying guanidino functions, with compounds of general formula VIII,

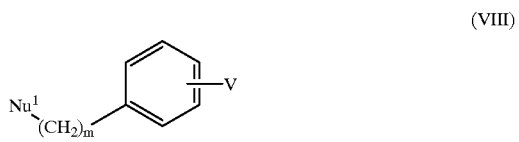

(VIII)

wherein m and V are as hereinbefore defined and $Nu^1$ denotes a leaving group, for example a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different, and, if necessary, subsequently cleaving protecting groups using the methods described hereinbefore.

The reaction is carried out in a suitable solvent, preferably in the presence of dipolar aprotic solvents such as dimethylsulphoxide, hexamethylphosphotriamide, 1,3-dimethyl-2-imidazolidinone, dimethylacetamide, dimethylformamide or N-methyl-2-pyrrolidinone at temperatures of between $-10°$ C. and $+50°$ C., but preferably at ambient temperature. The alkali metal salts of the carboxylic acids of general formula II are preferably produced in situ by the action of alkali metal carbonates, e.g. potassium or caesium carbonate, alkali metal hydroxides, e.g. sodium hydroxide, or alkali metal hydrides, e.g. sodium hydride, on the compounds of general formula II, before the compounds of general formula VIII are added (cf. also: J. E. Shaw, D. C. Kunerth and J. J. Sherry, Tetrahedron Letters 1973, 689–692; A. M. MacLeod, K. J. Merchant, M. A. Cascieri, P. Sadowski, E. Ber, C. J. Serain and R. Baker, J. Med. Chem. 36, 2044–2045 (1993); A. Rosowsky, R. A. Forsch. Ch.-P. Yu, H. Lazarus and G. P. Beardsley, J. Med. Chem. 27, 605–609 (1984)).

e) Reacting compounds of general formula IX,

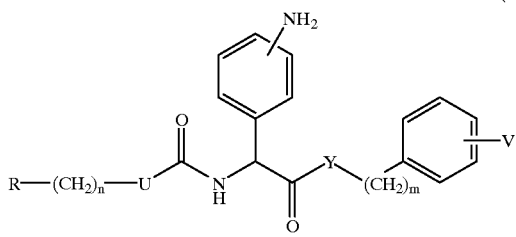

wherein
R, U, V, Y, m and n are as hereinbefore defined,
with carbonic acid derivatives of general formula X,

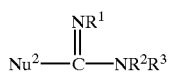

wherein
$R^1$, $R^2$ and $R^3$ are as hereinbefore defined and $Nu^2$ is a leaving group, for example an alkoxy, alkylthio, alkylsulphynyl or alkylsulphonyl group each with 1 to 10 carbon atoms in the alkyl moiety, e.g. the methoxy, ethoxy, methylthio, ethylthio, methylsulphynyl, ethylsulphynyl, propylsulphynyl, isopropylsulphynyl, methylsulphonyl or ethylsulphonyl group, the chlorine atom, the $SO_2H$, $SO_3H$ or $OPOCl_2$ group, or the group of general formula XI,

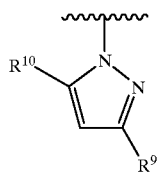

wherein
$R^9$ and $R^{10}$, which may be identical or different, denote hydrogen atoms or alkyl groups with 1 to 3 carbon atoms.

Occasionally, for example if $Nu^2$ is an alkoxy group, it is advantageous to use, instead of the compounds of general formula X, the inorganic acid salts thereof, e.g. the neutral sulphates or the hydrochlorides thereof.

The reactions are carried out analogously to processes known from the literature (cf. G. B. L. Smith, J. Amer. Chem. Soc. 51, 476 [1929]; B. Rathke, Chem. Ber. 17, 297 [1884]; R. Phillips and H. T. Clarke, J. Amer. Chem. Soc. 45, 1755 [1923]; S. J. Angyal and W. K. Warburton, J. Amer. Chem. Soc. 73, 2492 [1951]; H. Lecher and F. Graf, Chem. Ber. 56, 1326 [1923]; J. Wityak, S. J. Gould, S. J. Hein and D. A. Keszler, J. Org. Chem. 52, 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51, 1882–1884 [1986]; A. E. Miller and J. J. Bischoff, Synthesis 1986, 777; R. A. B. Bannard, A. A. Casselman, W. F. Cockburn and G. M. Brown, Can. J. Chem. 36, 1541 [1958]; Aktieselskabet Grea, Copenhagen, DE 28 26 452-C2; K. Kim, Y-T. Lin and H. P. Mosher, Tetrah. Letters, 29, 3183–3186 [1988]; H. B. Arzeno et al., Synth. Commun. 20, 3433–3437 [1990]; H. Bredereck and K. Bredereck, Chem. Ber. 94, 2278 [1961]; H. Eilingsfeld, G. Neubauer, M. Seefelder and H. Weidinger, Chem. Ber. 97, 1232 [1964]; P. Pruszynski, Can. J. Chem. 65, 626 [1987]; D. F. Gavin, W. J. Schnabel, E. Kober and M. A. Robinson, J. Org. Chem. 32, 2511 [1967]; N. K. Hart, S. R. Johns, J. A. Lamberton and R. I. Willing, Aust. J. Chem. 23, 1679 [1970]; CIBA Ltd., Belgian Patent 655 403; Chem. Abstr. 64, 17481 [1966]; J. P. Greenstein, J. Org. Chem. 2, 480 [1937]; F. L. Scott and J. Reilly, J. Amer. Chem. Soc. 74, 4562 [1952]; W. R. Roush and A. E. Walts, J. Amer. Chem. Soc. 106, 721 [1984], M. P. Bernatowicz, Y. Wu and G. R. Matsueda, J. Org. Chem. 57, 2497–2502 [1992]; H. Tsunematsu, T. Imamura and P. Makisumi, J. Biochem. 94, 123–128 [1983]) at temperatures of between 0° C. and +100° C., preferably +40° C. and +80° C., and using inert solvents, for example dichloromethane, tetrahydrofuran, 1,4-dioxan, acetonitrile, dimethylformamide, dimethylacetamide, N-methylpyrrolidone or mixtures thereof and—depending on the nature of the $Nu^2$ group—often in the presence of auxiliary bases, particularly alkali metal carbonates such as sodium or potassium carbonate, or tertiary amines, preferably N-ethyldiisopropylamine or triethylamine.

f) Reacting the uronium salts or thiuronium salts of general formula XII,

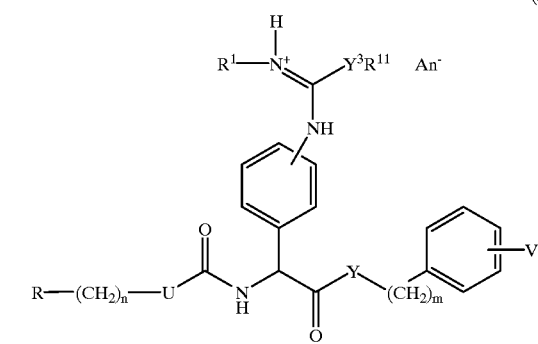

wherein
R, $R^1$, U, V, Y, n and m are as hereinbefore defined, $R^{11}$ denotes an alkyl group with 1 to 4 carbon atoms or the phenyl group, $Y^3$ denotes the oxygen or sulphur atom and $An^-$ denotes a monovalent anion, for example a chloride, bromide, iodide, methylsulphate, methanesulphonate or toluenesulphonate anion and ½ $SO_4^{2-}$, or the corresponding free isoureas or isothioureas
with amines of general formula XIII, $R^2R^3NH$            (XIII)

wherein $R^2$ and $R^3$ are as hereinbefore defined.

The reaction is carried out at temperatures of between 0 and 110° C., preferably between +15 and +60° C., and optionally in a suitable solvent, for example in water, dimethylformamide, dimethylacetamide, dimethylsulphoxide, N-methylpyrrolidone, tetrahydrofuran, dioxan, an alcohol such as methanol or ethanol or in a mixture thereof, whilst the compounds of general formula I are obtained directly as salts with the acid HAn. If instead of the uronium salts or thiuronium salts XII the fundamental bases, the corresponding free isoureas or isothioureas are used in the reaction, 1 equivalent of a weak acid, preferably acetic acid, must be added to the mixture.

g) For preparing compounds of general formula I wherein U denotes the oxygen atom or the —NH group:
Reacting isocyanates of general formula XIV,

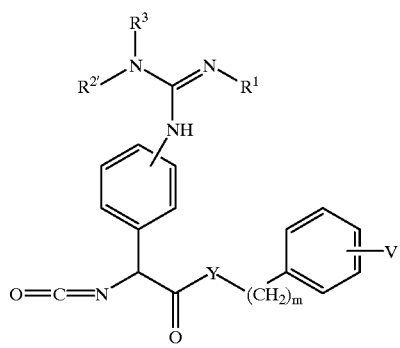

(XIV)

wherein $R^1$, $R^3$, V, Y and m are as hereinbefore defined and $R^{2'}$ has the meanings given for $R^2$ hereinbefore or also denotes one of the protecting groups mentioned hereinbefore for the protection of the side chains carrying guanidino functions, with compounds of general formula XV,

wherein

R and n are as hereinbefore defined and $U^1$ denotes the oxygen atom or the —NH— group, and, if necessary, subsequently cleaving protecting groups using the methods described hereinbefore.

The reaction is carried out at temperatures of between 0° C. and 150° C., preferably between 20° C. and 100° C., and optionally in the presence of anhydrous solvents, e.g. tetrahydrofuran, 1,4-dioxan, dimethylformamide, dimethylacetamide, N-methyl-2-pyrrolidone or 1,3-dimethyl-2-imidazolidinone or mixtures thereof.

h) For preparing compounds of general formula I wherein U represents the —NH— group:
Reacting isocyanates of general formula XVI,

wherein

R and n are as hereinbefore defined,
with α-amino acid derivatives of general formula V,

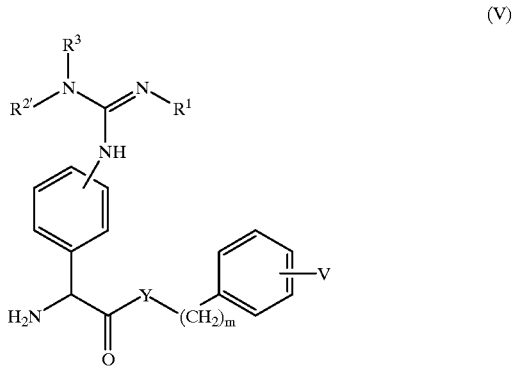

(V)

wherein
$R^1$, $R^3$, V, Y and m are as hereinbefore defined and $R^{2'}$ has the meanings given for $R^2$ hereinbefore or also denotes one of the protecting groups mentioned hereinbefore for the protection of the side chains carrying guanidino functions, and, if necessary, subsequently cleaving protecting groups using the methods described hereinbefore.

The reaction is carried out at temperatures of between 0 and 150° C., preferably at temperatures of between 20 and 100° C., and optionally in the presence of anhydrous solvents, e.g. tetrahydrofuran, 1,4-dioxan, dimethylformamide, dimethylacetamide, N-methyl-2-pyrrolidone or 1,3-dimethyl-2-imidazolidinone.

i) For preparing compounds of general formula I wherein V denotes the group —$(CH_2)_o$—$Y^1$—W—$Y^2$ wherein
o and W are as hereinbefore defined,
$Y^1$ represents the oxygen atom or the group —$NR^5$, in which
$R^5$ denotes a hydrogen atom or a straight-chained or branched alkyl group with 1 to 6 carbon atoms, and
$Y^2$ denotes a straight-chained or branched alkyl group with 1 to 10 carbon atoms optionally substituted by a hydroxy, alkoxycarbonyl or aminocarbonyl group, a cycloalkyl group with 4 to 10 carbon atoms, a straight-chained or branched alkoxy group with 1 to 5 carbon atoms, an aminoalkyl, alkylaminoalkyl, dialkylaminoalkyl, phenylmethoxy or 2-phenylethoxy group, a phenyl or phenylalkyl group with 1 to 3 carbon atoms in the alkyl moiety optionally mono-, di- or trisubstituted in the phenyl moiety by fluorine, chlorine or bromine atoms, by methyl, trifluoromethyl, cyano, amino, hydroxy, methoxy, acetyl, acetylamino, aminocarbonyl, methylaminocarbonyl or dimethylaminocarbonyl groups, or
the —$NR^6R^7$ group wherein
$R^6$ denotes a hydrogen atom, a straight-chained or branched alkyl group with 1 to 6 carbon atoms optionally substituted by a hydroxy, carboxy, alkoxycarbonyl or dialkylamino group with the proviso that the hydroxy group is not bound in the 1-position of the alkyl group, a cycloalkyl group with 4 to 8 carbon atoms or a phenyl, phenylmethyl, 2-phenylethyl or 3-phenylpropyl group optionally mono-, di- or trisubstituted in the phenyl moiety by fluorine, chlorine or bromine atoms, by methyl, trifluoromethyl, hydroxy, methoxy, amino, acetylamino, aminocarbonyl, methylaminocarbonyl, dimethylaminocarbonyl or cyano groups, whilst the substituents may be identical or different, or an alkanoyl, benzoyl, phenylalkanoyl, alkoxycarbonyl or aminocarbonyl group and $R^7$ has the meanings given for $R^6$ with the exception of a phenyl, alkanoyl, benzoyl, phenylalkanoyl, alkoxycarbonyl or aminocarbonyl group:

Transforming compounds of general formula XVII,

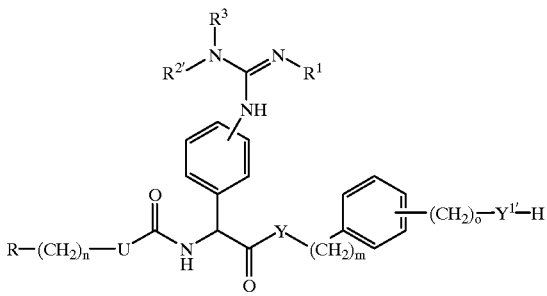

(XVII)

wherein m, n, o, R, $R^1$, $R^3$, U and Y are as hereinbefore defined, $R^{2'}$ has the meanings given for $R^2$ hereinbefore or also denotes one of the protecting groups mentioned hereinbefore for the protection of the side chains carrying guanidino functions and $Y^{1'}$ denotes the oxygen atom or the group —$NR^5$, wherein $R^5$ represents the hydrogen atom or a straight-chained or branched alkyl group with 1 to 6 carbon atoms, at the ($Y^{1'}$—H) function and, if necessary, subsequently cleaving protecting groups using the methods described hereinbefore and/or further transforming the group V obtained in the first instance.

The transformation at the ($Y^{1'}$—H) function may, depending on the reagent used, be carried out either without a solvent or in a suitable solvent, e.g. in water, alcohols such as methanol, ethanol or propanol, in N-methylpyrrolidinone, dimethylformamide or dimethylacetamide or mixtures thereof, optionally in the presence of inorganic acids, for example hydrochloric acid or sulphuric acid, organic or inorganic bases, for example triethylamine, Hunig base or sodium carbonate, and may optionally be followed by treatment with ammonia, with inorganic acids such as hydrochloric acid or sulphuric acid or with organic acids such as trifluoroacetic acid, at temperatures of between 0 and 150° C., preferably between 20 and 100° C.

Preferably by reacting compounds of general formula XVII wherein $Y^{1'}$ is the —$NR^5$ group, whilst $R^5$ represents the hydrogen atom or a straight-chained or branched alkyl group with 1 to 6 carbon atoms, with alkali metal cyanates, e.g. sodium cyanate, in the presence of strong acids, e.g. hydrochloric acid or aqueous trifluoroacetic acid, compounds of general formula I are obtained wherein V denotes the group —$(CH_2)_o$—$NR^5$—CO—$NH_2$, whilst o is as hereinbefore defined and $R^5$ represents a hydrogen atom or a straight-chained or branched alkyl group with 1 to 6 carbon atoms (cf. also: Org. Synth., Coll. Vol. IV, P. 515), by reaction with acetic anhydride in alcohols, e.g. in ethanol, compounds of general formula I are obtained wherein V denotes the group —$(CH_2)_o$—$NR^5$—CO—$CH_3$, whilst o is as hereinbefore defined and $R^5$ represents a hydrogen atom or a straight-chained or branched alkyl group with 1 to 6 carbon atoms, by reaction with ethyl chlorocarbonate in the presence of triethylamine, compounds of general formula I are obtained wherein V denotes the group —$(CH_2)_o$—$NR^5$—CO—$OC_2H_5$, whilst o is as hereinbefore defined and $R^5$ represents a hydrogen atom or a straight-chained or branched alkyl group with 1 to 6 carbon atoms, by reaction with N-(tert.butyl)-chlorsulphonic acid amide, compounds of general formula I are obtained wherein V represents the group —$(CH_2)_o$—$NR^5$—$SO_2$—NH—C$(CH_3)_3$, and by subsequent treatment with trifluoroacetic acid, compounds of general formula I are obtained wherein V denotes the group —$(CH_2)_o$—$NR^5$—$SO_2$—$NH_2$, whilst o is as hereinbefore defined and $R^5$ represents a hydrogen atom or a straight-chained or branched alkyl group with 1 to 6 carbon atoms, whilst it should be noted that if the group $R^{2'}$ denotes the Pmc protecting group, this is also removed, by reaction with benzoyl chloride, compounds of general formula I are obtained wherein V represents the group —$(CH_2)_o$—$NR^5$—CO—$C_6H_5$, whilst o is as hereinbefore defined and $R^5$ represents a hydrogen atom or a straight-chained or branched alkyl group with 1 to 6 carbon atoms, by reaction with methyl isocyanate, compounds of general formula I are obtained wherein V represents the group —$(CH_2)_o$—$NR^5$—CO—NH—$CH_3$, whilst o is as hereinbefore defined and $R^5$ represents a hydrogen atom or a straight-chained or branched alkyl group with 1 to 6 carbon atoms, by reaction with dimethylcarbamoyl chloride, compounds of general formula I are obtained wherein V represents the group —$(CH_2)_o$—$NR^5$—CO—$N(CH_3)_2$, whilst o is as hereinbefore defined and $R^5$ represents a hydrogen atom or a straight-chained or branched alkyl group with 1 to 6 carbon atoms, by reaction with nitrobiuret, compounds of general formula I are obtained wherein V represents the group —$(CH_2)_o$—$NR^5$—CO—NH—CO—$NH_2$, whilst o is as hereinbefore defined and $R^5$ denotes a hydrogen atom or a straight-chained or branched alkyl group with 1 to 6 carbon atoms, (see also: T. L. Davis et al, J. Am. Chem. Soc. 51, 1801–1806 (1929)) and by reacting compounds of general formula XVII wherein $Y^{1'}$ denotes the oxygen atom with phenyl chlorocarbonate and subsequent aminolysis, compounds of general formula I are obtained wherein V denotes the group —$(CH_2)_o$—O—CO—$NH_2$, whilst o is as hereinbefore defined (see also: G. R. Allen, Jr., J. F. Poletto and M. J. Weiss, J. Org. Chem. 30, 2897–2904 (1965)).

j) For preparing compounds of general formula I wherein $R^1$ denotes a branched or unbranched aliphatic alkylcarbonyl group containing 2 to 5 carbon atoms, which may be substituted in the alkyl moiety by an alkoxycarbonyl or phenylalkoxycarbonyl group, by a phenyl group or by a 5- or 6-membered heteroaromatic ring linked via a carbon atom, or denotes a benzoyl group wherein the phenyl moiety may also be replaced by a 5 or 6-membered heteroaromatic ring linked via a carbon atom, whilst the abovementioned 5-membered heteroaromatic rings may contain a nitrogen, an oxygen or sulphur atom or a nitrogen atom and an additional oxygen, sulphur or further nitrogen atom and may also be substituted at a nitrogen atom by an alkyl group, the 6-membered heteroaromatic rings contain 1, 2 or 3 nitrogen atoms and the abovementioned phenyl groups may additionally be mono-, di- or at most trisubstituted, as may all the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different:

Reacting compounds of general formula XVIII,

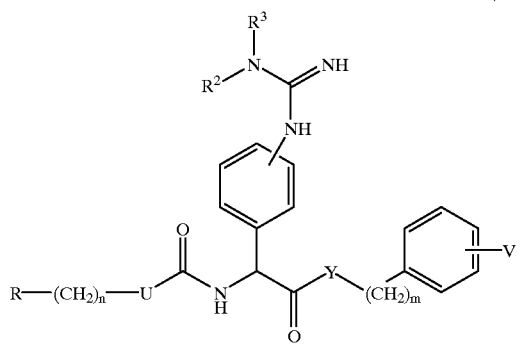

(XVIII)

wherein R, $R^2$, $R^3$, U, V, Y, n and m are as hereinbefore defined,
with a compound of general formula XIXa, $R^{1'}$—CO—Nu        (XIXa)

wherein $R^{1'}$ denotes a branched or unbranched alkyl group containing 1 to 4 carbon atoms, which may be substituted by an alkoxycarbonyl or phenylalkoxycarbonyl group, by a phenyl group or by a 5- or 6-membered heteroaromatic ring linked via a carbon atom, a phenyl group or a 5- or 6-membered heteroaromatic ring linked via a carbon atom, whilst the abovementioned 5-membered heteroaromatic rings may contain a nitrogen, an oxygen or a sulphur atom or a nitrogen atom and an additional oxygen, sulphur or further nitrogen atom and may also be substituted at a nitrogen atom by an alkyl group, the 6-membered heteroaromatic rings may contain 1, 2 or 3 nitrogen atoms and the abovementioned phenyl groups may additionally be mono-, di- or at most trisubstituted, as may all the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different, and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethylphosphotriamide, sulfolane, 1,3-dimethyl-2-imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20 ° C. and +60° C., most preferably between +15° C. and +30° C. Any acylatable functions present in group V are included in this reaction. Any reaction products diacylated in the guanidino function of the side chain and obtained as by-products can generally be separated quite easily using conventional chromatographic methods.

k) For preparing compounds of general formula I wherein $R^1$ denotes the aminocarbonyl group, which may be mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, diphenylalkyl, phenyl, cycloalkyl or cycloalkylalkyl groups each with 3 to 8 carbon atoms in the ring, whilst the substituents may be identical or different and the abovementioned phenyl groups may in turn, independently of one another, be mono- or disubstituted by fluorine, chlorine or bromine atoms, methyl, methoxy, alkoxycarbonylmethoxy, hydroxy or trifluoromethyl groups:

Reacting compounds of general formula XVIII,

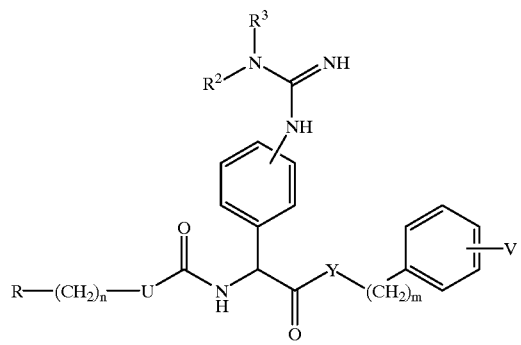

(XVIII)

wherein
R, $R^2$, $R^3$, U, V, Y, n and m are as hereinbefore defined,
with a compound of general formula XIXb, $R^{1''}$—N=C=O        (XIXb)

wherein $R^{1''}$ denotes an alkyl, phenylalkyl, (1-naphthyl)alkyl, (2-naphthyl)alkyl, alkoxycarbonylalkyl, phenylalkoxycarbonylalkyl, phenoxycarbonylalkyl, diphenylalkyl, phenyl, cycloalkyl or cycloalkylalkyl groups each with 3 to 8 carbon atoms in the cycloalkane ring, whilst the abovementioned phenyl groups may in turn be mono- or disubstituted independently of one another by fluorine, chlorine or bromine atoms, methyl, methoxy, alkoxycarbonylmethoxy, hydroxy or trifluoromethyl groups, and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethylphosphotriamide, sulfolane, 1,3-dimethyl-2-imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20° C. and +60° C., most preferably between +15° C. and +30° C. Any acylatable functions present in group V are included in this reaction. Any reaction products obtained as by-products which are dicarbamoylated in the guanidino function of the side chain can generally be separated off quite easily using conventional chromatographic methods.

l) For preparing compounds of general formula I wherein

R¹ denotes an alkoxycarbonyl or phenylalkoxycarbonyl group, whilst the phenyl moiety may in its turn be mono- or disubstituted by fluorine, chlorine or bromine atoms, methyl, methoxy, alkoxycarbonylmethoxy, hydroxy or trifluoromethyl groups and the substituents in each case may be identical or different:

Reacting compounds of general formula XVIII,

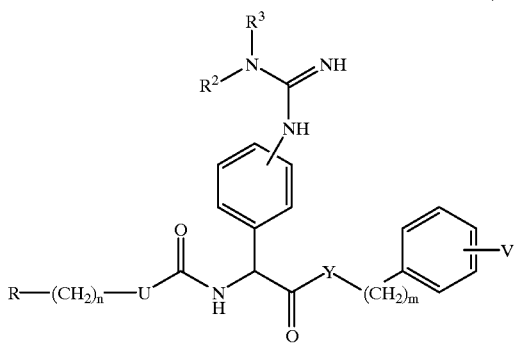

(XVIII)

wherein
R, R², R³, U, V, Y, n and m are as hereinbefore defined, with a compound of general formula XIXC,

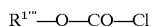

R¹'''—O—CO—Cl    (XIXC)

wherein
R¹''' denotes an alkyl or phenylalkyl group, in which the phenyl moiety may in its turn be mono- or disubstituted by fluorine, chlorine or bromine atoms, methyl, methoxy, alkoxycarbonylmethoxy, hydroxy or trifluoromethyl groups, whilst the substituents in each case may be identical or different, and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethyl phosphotriamide, sulfolane, 1,3-dimethyl-2-imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20° C. and +60° C., most preferably between +15° C. and +30° C. Any acylatable functions present in group V are included in this reaction. Any reaction products obtained as by-products which are diacylated in the guanidino function of the side chain can generally be separated off quite easily using conventional chromatographic methods.

m) For preparing the compounds of general formula XX covered by general formula I

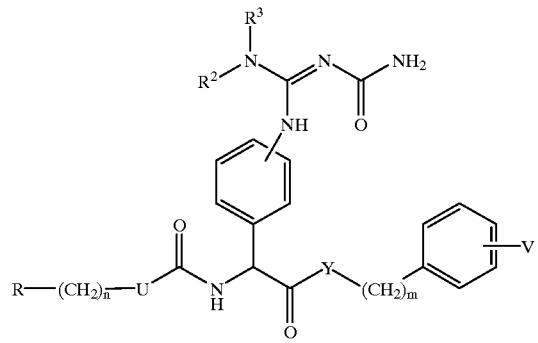

(XX)

wherein

R, R², R³, U, V, Y, n and m are as hereinbefore defined:

Partial hydrolysis of cyanoguanidines of general formula XXI,

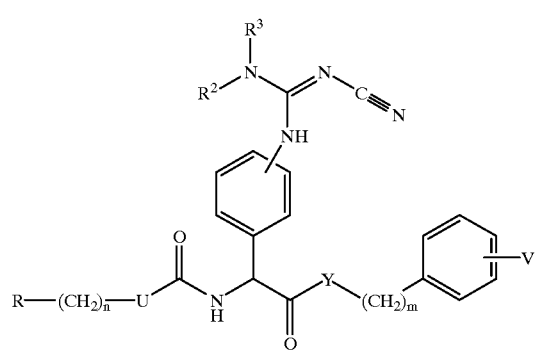

(XXI)

wherein

R, R², R³, U, V, Y, n and m are as hereinbefore defined, by the action of strong aqueous acids, preferably aqueous trifluoroacetic acid, at temperatures of between 0° C. and +70° C., preferably +15° C. and +45° C. (see also: P. Theobald, J. Porter, C. Rivier, A. Corrigan, W. Hook, R. Siraganian, M. Perrin, W. Vale and J. Rivier, J. Med. Chem. 34, 2395–2402 (1991); P. J. Garratt, P. N. Thorn and R. Wrigglesworth, Tetrahedron 49, 6885–6898 (1993)). Water-miscible cosolvents, for example tetrahydrofuran or dioxan, may be added to the reaction mixture, but the reaction will also succeed in the absence of any additional solvents.

n) For preparing the compounds of general formula XXII covered by general formula I, (XXII)

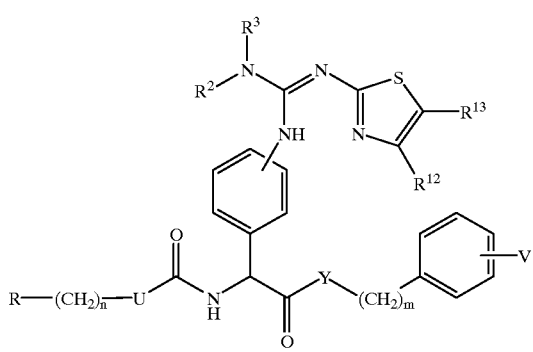

wherein R, R², R³, U, V, Y, m and n are as hereinbefore defined and R¹² and R¹³ independently of one another represent a hydrogen atom, an alkyl group with 1 to 5 carbon atoms, a cycloalkyl group with 3 to 8 carbon atoms or a phenylalkyl group with 1 to 5 carbon atoms in the alkyl moiety, whilst these groups may be identical or different:

Converting cyanoguanidines of general formula

XXI

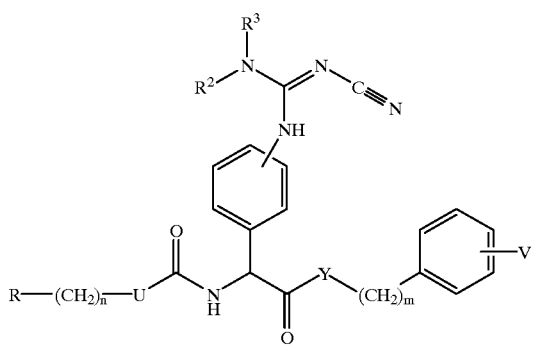

wherein R, R², R³, U, V, Y, n and m are as hereinbefore defined, into aminothiocarbonylguanidines of general formula XXIII, (XXIII)

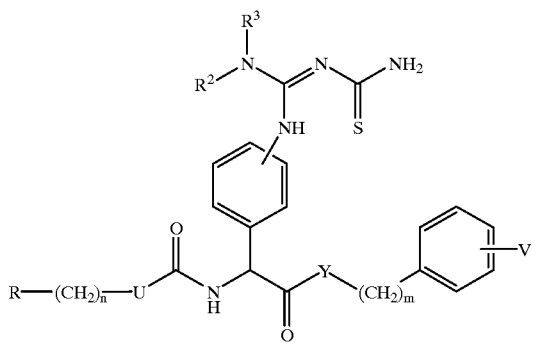

wherein R, R², R³, U, V, Y, n and m are as hereinbefore defined, and subsequently reacting with α-halocarbonyl compounds of general formula XXIV,

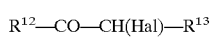 (XXIV)

wherein R¹² and R¹³ independently of one another represent a hydrogen atom, an alkyl group with 1 to 5 carbon atoms, a cycloalkyl group with 3 to 8 carbon atoms or a phenylalkyl group with 1 to 5 carbon atoms in the alkyl moiety, whilst these groups may be identical or different, and Hal denotes a chlorine, bromine or iodine atom, under the conditions of a thiazole synthesis according to Hantzsch. If for example a chloromethylketone of general formula $R^{12}$—CO—$CH_2$—Cl, wherein $R^{12}$ is as hereinbefore defined, is used as the halocarbonyl compound, thiazoles of general formula XXIIa are obtained, (XXIIa)

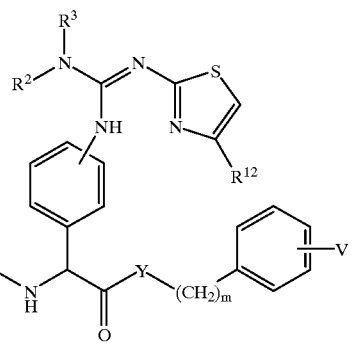

but if an α-haloaldehyde of general formula $R^{12}$—CHHal—CH=O wherein $R^{12}$ is as hereinbefore defined is used, or more appropriately a mixture of an aldehyde of general formula $R^{12}$—$CH_2$—CH=O and iodine is used, which in situ forms the α-iodoaldehyde required, thiazoles of general formula XXIIb are obtained.

(XXIIb)

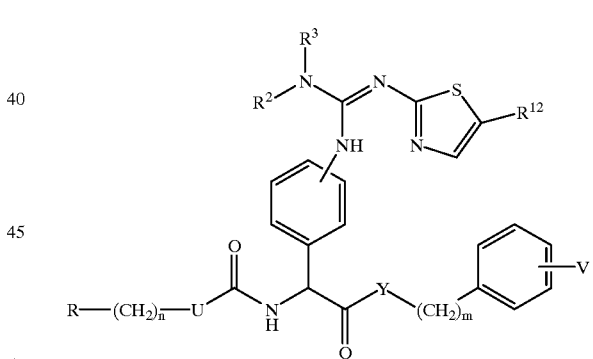

The conversion of the cyanoguanidines of general formula XXI into the aminothiocarbonylguanidines of general formula XXIII is most easily carried out by treating with hydrogen sulphide at temperatures of between ambient temperature and 100° C., preferably between 40° C. and 80° C. (cf. also: F. Kurzer, J. Chem. Soc. 1955, 1–6; Org. Synth., Coll. Vol. 4, 502–504 (1963)). Pyridine is the preferred solvent for this reaction. The reaction of the aminothiocarbonyl compounds of general formula XXII to obtain the thiazoles of general formula XXII is preferably carried out in boiling acetone and first yields the hydrohalic acid salts of the thiazoles of general formula XXII, which are only converted into the free bases in the course of working up, particularly during column or flash chromatography in the presence of ammonia-containing eluants. The reaction may, however, also be carried out in the presence of weak inorganic bases, particularly sodium hydrogen carbonate, and then directly yields the free bases of general formula XXII.

o) For preparing compounds of general formula I wherein U denotes the oxygen atom:

Aminolysis of chlorocarbonates of general formula XXV,

R—(CH$_2$)$_n$—O—CO—Cl    (XXV)

wherein

R and n are as hereinbefore defined, with α-amino acid derivatives of general formula XXVI,

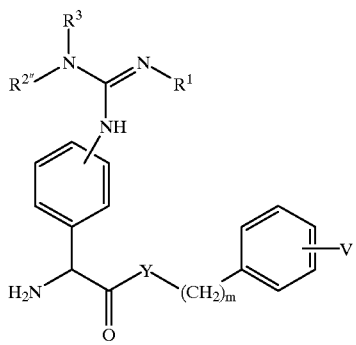

(XXVI)

wherein

R$^1$, R$^3$, V, Y and m are as hereinbefore defined and R$^{2''}$ has the meanings given for R$^2$ hereinbefore or also denotes one of the protecting groups mentioned hereinbefore for protecting guanidino functions present in the side chain which are orthogonal to carbamates and, if necessary, subsequently cleaving protecting groups using the methods described hereinbefore.

The reaction is carried out at temperatures of between 0 and 150° C., preferably at temperatures of between 20 and 100° C., and optionally in the presence of anhydrous solvents, e.g. tetrahydrofuran, 1,4-dioxan, dimethylformamide, dimethylacetamide, N-methyl-2-pyrrolidone or 1,3-dimethyl-2-imidazolidinone or mixtures thereof, and in the presence of auxiliary bases. The auxiliary bases used may be alkali metal carbonates, e.g. sodium carbonate, potassium carbonate or caesium carbonate, alkali metal acetates, e.g. sodium or potassium acetate, but preferably tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]-undec-7-ene.

p) In order to prepare compounds of general formula I wherein R$^1$, R$^2$ and R$^3$ denote hydrogen atoms:

Reacting compounds of general formula IX,

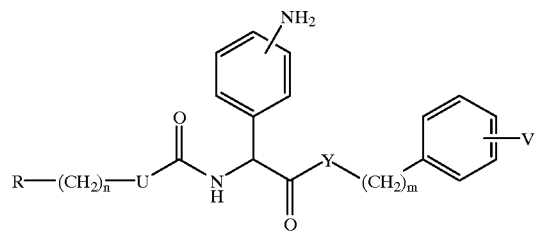

(IX)

wherein
R, U, V, Y, n and m are as hereinbefore defined, with cyanamide.

The reactions are carried out at temperatures of between 20° C. and 150° C, optionally in an autoclave. The solvents used are alcohols such as methanol, ethanol or n-propanol, ethers such as dioxan or esters such as ethyl acetate. Water may be used as another cosolvent. Although the reaction will succeed without the addition of acids, it is preferably carried out in the presence of organic acids, e.g. acetic acid, and especially strong acids, e.g. methanesulphonic acid, sulphuric acid, hydrogen bromide, hydrogen chloride or hydrochloric acid. If, for example, the salts of the amines of general formula IX are used in the reaction, the compounds of general formula I are obtained in the form of the corresponding salts (cf. also: Houben-Weyl, Methoden der Organischen Chemie, 4th edition, Georg-Thieme-Verlag, Stuttgart, 1952 onwards, volume VIII, p. 98, p. 180; Ullmanns Encyclopadie der Technischen Chemie, Verlag Chemie, Weinheim, 1972–1977, volume VIII, p. 328; E. H. Sheers, Kirk-Othmer Encycl. Chem. Technol., 2nd ed., 10, 734 [1966]; A. Kampf, Chem. Ber. 37, 1681 [1904]; R. A. Corral, O. O. Orazi and M. F. de Petruccelli, Chem. Commun. 1970, 556).

q) In order to prepare compounds of general formula I wherein R$^1$ denotes a hydrogen atom:

Reacting cyanamides of general formula XXVII,

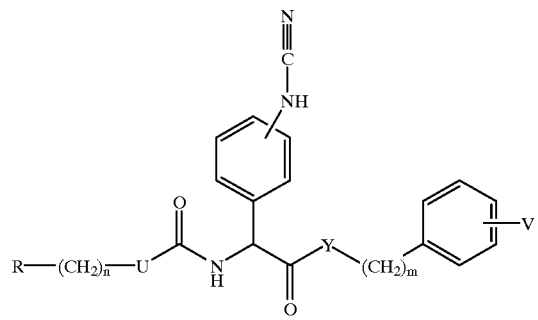

(XXVII)

wherein R, U, V, Y, m and n are as hereinbefore defined, with inorganic acid salts of ammonia or amines of general formula XIII, wherein R$^2$ and R$^3$ are as hereinbefore defined.

The reaction is carried out using suitable solvents, e.g. lower alcohols such as methanol and ethanol or mixtures thereof, at temperatures of between +10 and +190° C., preferably between 90 and 160° C. Examples of salt-forming acids include hydrochloric acid, hydrobromic acid, hydriodic acid, sulphuric acid, phosphoric acid, methanesulphonic acid or p-toluenesulphonic acid. The reaction is preferably carried out using equivalent quantities of the ammonium salt and in the presence of additional free ammonia or free amine of general formula XIII, but will also work in the absence of these free bases.

The amino acid derivatives of general formula I according to the invention contain at least one chiral centre. If in addition the group R is prochiral or chiral, the compounds may occur in the form of two diastereomeric pairs of antipodes. The invention includes the individual isomers as well as the mixtures thereof.

The diastereomers are separated on the basis of their different physico-chemical properties, e.g. by fractional crystallisation from suitable solvents, by high pressure liquid or column chromatography using chiral or preferably achiral stationary phases.

The racemates of general formula I may be separated for example by HPLC on suitable chiral stationary phases (e.g. Chiral AGP, Chiralpak AD). Racemates which contain a basic function may also be separated by means of the diastereomeric, optically active salts which are formed on reacting with an optically active acid, for example (+)-or (−)-tartaric acid, (+) or (−)-diacetyltartaric acid, (+) or (−)-monomethyl tartrate or (+)-camphorsulphonic acid.

According to a conventional method of isomer separation the racemate of a compound of general formula I is reacted with one of the abovementioned optically active acids in equimolar amounts in a solvent and the crystalline, diastereomeric, optically active salts obtained are separated using their differences in solubility. This reaction may be carried out in any kind of solvent provided that it exhibits a sufficient difference in terms of the solubility of the salts. Preferably, methanol, ethanol or the mixtures thereof are used, for example in a ratio by volume of 50:50. Then each of the optically active salts is dissolved in water, neutralised with a base, such as sodium carbonate or potassium carbonate, sodium hydroxide solution or potassium hydroxide solution and the corresponding free compound is obtained in the (+) or (−) form.

Only the (R)-enantiomer or a mixture of two optically active, diastereomeric compounds of general formula I is obtained by carrying out the above-described syntheses with a reaction component containing the corresponding (R)-configured amino acid.

The starting materials of general formulae III, IV, V, VI, VII, VIII, IX, X, XI, XIII, XV, XVI, XIXa, XIXb, XIXc, XXIV, XXV, XXVI and XXVII required for synthesising the compounds of general formula I are commercially obtainable or may be prepared by methods known from the literature. The acids II are obtained for example under the conditions of a Schotten-Baumann reaction from the corresponding α-amino acids and compounds of general formulae III (cf. also: M. Bodanszky and A. Bodanszky, "The Practice of Peptide Synthesis", Springer Verlag 1984, P. 9 to 30). The α-amino-nitrobenzeneacetic acids required as essential starting materials for synthesising the compounds of general formula I are also known from the literature (cf. e.g.: P. Friis and A. Kjaer, Acta Chem. Scand. 17, 2391–2396 (1963); J. Plochl and W. Loe, Ber. dtsch. chem. Ges. 18, 1179–1182 (1885); Beecham Group, Belgian Patent 662478.

Isocyanates of general formula XIV may readily be prepared from α-amino acid derivatives of general formula V or from the hydrochlorides thereof by reacting with phosgene, diphosgene or triphosgene in the presence of pyridine (cf. also: J. P. Nowick, N. A. Powell, T. M. Nguyen and G. Noronha, J. Org. Chem. 57, 7364–7366 [1992]).

The uronium salts of general formula XII are most easily obtained by adding $R^1$—OH alcohols to the corresponding cyanamides, for example using potassium cyanide (cf. also: A. Donetti et al., Tetrah. Lett. 1969, 3327–3328; A. Donetti et al., J. Org. Chem. 37, 3352–3353 (1972); M. Okahara et al., Tetrah. Lett. 1981, 4105–4106) or sodium methoxide (cf. also: F. C. Schaefer et al., J. Org. Chem. 26, 412–418 (1961); R. M. Giuliano et al., J. Org. Chem. 51, 2304–2307 (1986); F. H. P. Hurd et al., J. Chem Soc. 1949, 1732–1738)) as catalysts, the thiuronium salts of general formula XII are obtained from corresponding thioureas by reaction with alkylating agents of type $R^{11}$—X, wherein X denotes, for example, the iodine atom or the groups $OSO_2CH_3$ or $OSO_2C_6H_4CH_3$ (p). The starting compounds of general formula XVII can easily be produced from precursors which carry, instead of the terminal group —$(CH_2)_o$—$Y^1$—H of general formula XVII, an end group —$(CH_2)_o$—$Y^{1'}$—Pg characterised by readily cleavable protecting groups Pg, e.g. tert.butoxycarbonyl or phenylmethoxycarbonyl, or precursor groups, for example —$(CH_2)_{o-1}$—C≡N or —$(CH_2)_o$NO_2$.

The starting compounds of general formula XVIII may be synthesised according to at least one of processes a) to o) described hereinbefore.

In order to synthesise cyanoguanidines of general formula XXI, diphenyl cyanocarbimidate is reacted successively with anilines of general formula IX and with amines of general formula XIII (cf. also R. L. Webb and C. S. Labaw, J. Het. Chem. 19, 1205 [1982]; R. L. Webb, D. S. Eggleston, C. S. Labaw, J. J. Lewis and K. Wert, J. Het. Chem. 24, 275 [1987]; P. Theobald, J. Porter, C. Rivier, A. Corrigan, W. Hook, R. Siraganian, M. Perrin, W. Vale and J. Rivier, J. Med. Chem. 34, 2395–2402 [1991]; J. Hirschfeld, A. Buschauer, S. Elz, W. Schunack, M. Ruat, E. Traiffort and J.-C. Schwartz, J. Med. Chem. 35, 2231–2238 [1992]).

(Aminothiocarbonyl)-guanidines of general formula XXIII can most easily be prepared by treating cyanoguanidines of general formula XXI with hydrogen sulphide (cf. also: F. Kurzer, J. Chem. Soc. 1955, 1–6; Org. Synth., Coll. Vol. 4, 502–504 [1963]).

The compounds of general formula I obtained may be converted into their physiologically acceptable salts with inorganic or organic acids, particularly for pharmaceutical applications. Examples of acids for this purpose include hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula I thus obtained, if they contain a carboxy group, may subsequently, if desired, be converted into the addition salts thereof with inorganic or organic bases, particularly, for pharmaceutical use, into the physiologically acceptable addition salts thereof. Suitable bases include for example sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have NPY-antagonistic properties and exhibit good affinities in NPY-receptor binding studies. The compounds exhibit NPY-antagonistic properties both in vivo and in vitro in the pharmacological test systems described hereinafter.

To demonstrate the affinity of compounds of general formula I for human NPY-receptors and their antagonistic properties the following experiments were carried out:

A. Binding Studies with SK-N-MC Cells (Expressing the Human $Y_1$-receptor)

The cells are detached by a mixture of 0.02% EDTA in PBS and resuspended in 10 ml of incubation medium (MEM/25 mM Hepes+0.5% BSA, 50 μM PMSF, 0.1% bacitracin, 3.75 mM $CaCl_2$) per approx. 40 million cells. After 5 min centrifugation (150×g) the pellet is resuspended in the same volume and after another washing step resuspended in 10 ml of incubation medium, counted and diluted down to 1.25 million cells/ml. Then 200 μl of a suspension of 1.25 million cells/ml are incubated for 3 hours at ambient temperature with 25 μl of a 300 pM solution of [$^{125}$I]-Bolton-Hunter-NPY and increasing concentrations ($10^{-11}$ to $10^{-6}$ M) of the test substances, maintaining a total volume of 250 μl. The incubation is ended by centrifugation (10 min at 3000×g and 4° C.). After washing once with PBS the radioactivity of the pellet is measured in the gamma-counter. The radioactivity thus obtained represents the sum of specific and non-specific binding of [$^{125}$I]-Bolton-Hunter-NPY. The amount of non-specific binding is defined as the radioactivity which is bound in the presence of 1 μM NPY. The $IC_{50}$ values of the unlabelled test substances are determined graphically. They represent the concentration of the relevant test substance at which the specific binding of [$^{125}$I]-Bolton-Hunter-NPY to the NPY-$Y_1$ receptor is inhibited by 50%.

The compounds of general formula I have $IC_{50}$-values of <10,000 nM in the test described.

B. In Vitro NPY-antagonism

Male rats (CHbb: THOM, 300 to 350 g) are given heparin (100 IU, i.v.) and the animals are then killed by a blow to the back of the neck. The abdomen is opened up along the centre of the body and the left kidney is removed, after the insertion of catheters in the renal artery, the renal vein and the ureter. The isolated kidney is immediately perfused with a modified Krebs-Ringer solution (4 ml/minute) of the following composition:

| | |
|---|---|
| NaCl | 118.0 mmol/l |
| $KH_2PO_4$ | 1.2 mmol/l |
| KCl | 4.8 mmol/l |
| $HgSO_4$ | 1.2 mmol/l |
| $CaCl_2$ | 2.5 mmol/l |
| $NaHCO_3$ | 25.0 mmol/l |
| Glucose | 6.5 mmol/l |

A mixture of 95% $O_2$/5% $CO_2$ is passed through the solution which is maintained at a temperature of 37° C. The perfusion pressure is measured continuously using a pressure recorder. After a 60-minute stabilising period the perfusion rate is adjusted so as to achieve a perfusion pressure of about 100 mm Hg. After another 30 minutes the experiment is started and NPY (1 mM) is administered as a bolus (0.1 ml) at 15 minute intervals until the pressure increase observed achieves a constant value. The compounds to be investigated are administered as a continuous infusion over a period of 5 minutes and then NPY is injected. After a 30-minute washing-out period the next-highest concentration of the test substance is investigated. For each test, 3 to 5 different concentrations of the relevant compound are tested. Concentration-activity-curves can be drawn by plotting the percentage inhibition of the NPY activity against the logarithm of the concentration (mol/l) of the compound.

The compounds of general formula I exhibit NPY-antagonistic properties in the in-vitro test model described, in a dosage range of between $10^{-8}$ and $10^{-5}$ M.

C. In-vivo-NPY Antagonism

Male rats with normal blood pressure (Chbb:THOM, 300 to 350 g) are anaesthetised with sodium hexobarbital (150 mg/kg, i.p.). After intubation of the trachea the animals are pithed by the insertion of a blunt needle through the eye into the central canal of the spinal cord. The animals are ventilated with oxygen-enriched ambient air using a ventilator pump (20 strokes per minute). A cannula is inserted into the left carotid artery and the arterial blood pressure is measured using a pressure transducer (Braun Melsungen Combitrans) attached to a recording instrument. For injection purposes a catheter through which heparin is administered (200 IU/kg, i.v.) is inserted in the left jugular vein,. After the blood pressure has been stabilised the animals are given 2 bolus injections of NPY (10 mg/kg, i.v.) at an interval of 15 minutes. The mean increase in diastolic blood pressure serves as a reference value (=100%). The test substances are injected in increasing doses (4 to 6 doses) at 15 minute intervals. One minute after the administration of the test substance NPY is given.

The antagonistic activity of the test substances is determined by plotting the percentage inhibition of the NPY-induced blood pressure effects against the logarithm of the concentration of active substance.

The compounds of general formula I display NPY-antagonistic properties in the in vivo test model after intravenous administration in a dosage range of 0.001 to 10 mg/kg.

In view of their pharmacological properties the compounds of general formula I and the physiologically acceptable salts thereof are thus suitable for treating cardiovascular diseases, e.g. for treating arterial hypertension, hypertensive crisis, stress-induced high blood pressure triggered, for example, by the environment, by physical exertion or cold irritation, chronic cardiac insufficiency, coronary heart disease, such as angina pectoris, myocardial infarct and syndrome X, and also for treating subarachnoid bleeding, vascular-hypertrophic changes, e.g. restenosis after coronary angioplasty (PCTA), cerebral and coronary vasospasms, e.g. stroke, chronic kidney failure, hyperthyroidism, obesity and diabetes, epileptic diseases and for diagnosing, evaluating the prognosis of and treating tumoral diseases, for example pheochromocytomas, neuro(fibro)blastomas, ganglioneuromas, ganglioneuroblastomas, rhabdomyosarcomas, malignant ectomesenchymomas, anaplastic astrocytomas or haemangioblastomas.

The dosage required to achieve the corresponding effect is appropriately, for intravenous administration, 0.01 to 3 mg/kg of body weight, preferably 0.1 to 1 mg/kg of body weight, and for oral administration 0.1 to 10 mg/kg of body weight, preferably 1 to 10 mg/kg of body weight, 1 to 3×a day.

For this purpose the compounds of general formula I prepared according to the invention, optionally in conjunction with other active substances, such as e.g. hypotensive agents, ACE-inhibitors, diuretics and/or calcium antagonists, together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethyleneglycol, propyleneglycol, cetylstearylalcohol, carboxy-methylcellulose or fatty substances such as hard fat or suitable mixtures thereof, may be incorporated in conventional galenic preparations such as plain or coated tablets, capsules, powders, suspensions or suppositories.

Additional active substances for the abovementioned combinations might thus include, for example, bendroflumethiazide, chlorothiazide, hydrochlorothiazide, spironolactone, benzthiazide, cyclothiazide, ethacrinic acid, furosemide, metoprolol, prazosine, atenolol, propranolol, (di)hydralazine-hydrochloride, diltiazem, felodipine, nicardipine, nifedipine, nisoldipine, nitrendipine, captopril, enalapril, lisinopril, cilazapril, quinapril, fosinopril and ramipril. The dosage for these active substances is conveniently from 1/5 of the minimum dose normally recommended up to 1/1 of the normally recommended dose, i.e. for example 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipine or 5 to 60 mg of nitrendipine.

The invention further relates to the use of the compounds of general formula I as valuable adjuvants for the production and purification (by affinity chromatography) of antibodies and, after suitable radiolabelling, for example by direct labelling with $^{125}$I or $^{131}$I or by tritiation of suitable precursors, for example by replacing halogen atoms with tritium, in RIA and ELISA assays and as a diagnostic or analytical aid in neutrotransmitter research.

The Examples which follow are intended to illustrate the invention:

Preliminary Remarks

"Mp." denotes "melting point", "D." denotes "decomposition". For all the compounds there are satisfactory elemental analyses, IR, UV, $^1$H-NMR and generally also mass spectra. Unless otherwise stated, $R_f$ values were determined using ready-made silica gel TLC plates 60 $F_{254}$ (E. Merck, Darmstadt, serial no. 5729) and an eluant consisting of n-butanol/glacial acetic acid/water=4/1/1 (v/v/v), without chamber saturation. If the configuration is not specified in detail it is unclear whether it is the (R)-enantiomer or whether partial or even total racemisation has occurred.

EXAMPLE 1

(R,S)-3-(Aminoiminomethylamino)-α-[(diphenylacetyl)amino]-N-[(4-hydroxyphenyl) methyl]-benzeneacetamide-hydrochloride a) (R,S)-α-[(Diphenylacetyl)amino]-3-nitrobenzeneacetic Acid To a suspension of 43.0 g (0.219 mol) of α-amino-3-nitrobenzeneacetic acid in a mixture of 400 ml of tetrahydrofuran and 200 ml of water was added a solution of 9.0 g (0.225 mol) of sodium hydroxide in 100 ml of water. To this mixture were then simultaneously added dropwise within 30 minutes a solution of 50.7 g (0.22 mol) of diphenylacetylchloride in 300 ml of tetrahydrofuran and a solution of 9.0 g (0.225 mol) of sodium hydroxide in 100 ml of water without any external cooling, the mixture was then stirred for a further 12 hours at ambient temperature and the solvents were then distilled off in a water jet vacuum. The oily residue remaining was dissolved in 50 ml of water and acidified with 200 ml of 1 N aqueous hydrochloric acid. The precipitate obtained was decocted with 300 ml of ethyl acetate, then kept for 5 hours at ambient temperature. 22.6 g (26% of theory) of pale yellow crystals were obtained, m.p. 238–243° C. (D.).

IR (KBr): 1645 (broad, amide-CO) cm$^{-1}$ b) (R,S)-α-[(diphenylacetyl)amino]-N-[(4-hydroxyphenyl)methyl]-3-nitrobenzeneacetamide To a solution of 7.8 g (20 mmol) of (R,S)-α-[(diphenylacetyl)amino]-3-nitrobenzeneacetic acid in a mixture of 20 ml of dimethylformamide and 120 ml of tetrahydrofuran were added successively 2.5 g (24.7 mmol) of triethylamine, 2.7 g (20 mmol) of HOBT, 6.72 g (20.93 mmol) of TBTU and 2.9 g (23.56 mmol) of 4-hydroxybenzenemethanamine and the mixture was stirred for 1 hour at ambient temperature. The mixture was largely freed from solvent in a water jet vacuum, stirred into 150 ml of water and then exhaustively extracted with ethyl acetate. The combined ethyl acetateextracts were dried over sodium sulphate and again freed from solvent in vacuo. 6.0 g (61% of theory) of a yellow crystalline product were obtained, m.p. 238–242° C., which was used in the following step without further purification.

IR (KBr):
1639.4 (amide-CO),
1525.0 (amide-II; aromatic NO$_2$),
1351.2 (NO$_2$) cm$^{-1}$ c) (R,S)-3-amino-α-[(diphenylacetyl)amino]-N-[(4-hydroxyphenyl)methyl]-benzeneacetamide The solution of 6.0 g (0.0121 mol) of (R,S)-α-[(diphenylacetyl)amino]-N-[(4-hydroxyphenyl)methyl]-3-nitrobenzeneacetamide in 500 ml of ethanol was hydrogenated for 16 hours in the presence of 2.0 g of Raney nickel as catalyst at a hydrogen pressure of 3.5 bar. The mixture was diluted with a further 250 ml of ethanol and suction filtered while hot to remove the catalyst. The colourless filtrate was evaporated down to a volume of 150 ml and after cooling mixed with the same volume of diethylether. After standing for three hours at ambient temperature the resulting crystals were suction filtered. 4.75 g (84% of theory) of colourless crystals were obtained, m.p. 215 –217° C.

IR (KBr): 1639.4 (amide-CO) cm$^{-1}$

MS: M$^+$=465 d) (R,S)-3-(aminoiminomethylamino)-α-[(diphenylacetyl)amino]-N-[(4-hydroxyphenyl)methyl]-benzeneacetamidehydrochloride The mixture of 2.3 g (4.94 mmol) of (R,S)-3-amino-α-[(diphenylacetyl)amino]-N-[(4-hydroxyphenyl)methyl]-benzeneacetamide, 5 ml of (5 mmol) of 1N aqueous hydrochloric acid and 250 ml of ethanol was refluxed for 5 minutes, the clear solution obtained was then evaporated down in vacuo. The residue was taken up in 250 ml of dioxan and after the addition of 0.34 g (8.1 mmol) of cyanamide refluxed for 7 hours. The residue remaining after distillation of the solvent was divided between water and dichloromethane. The dichloromethane phase was discarded, the aqueous phase was filtered through a glass fiber filter, the residue thus obtained was dried in vacuo and yielded 2.58 g (96% of theory) of a colourless, substantially amorphous product, $R_f$ 0.79.

IR (KBr): 1652.9 (broad, amide-CO) cm$^{-1}$

MS: (M+H)$^+$=508

EXAMPLE 2

(R,S)-N-[[4-(aminocarbonylaminomethyl)phenyl] methyl]-3-(amino-iminomethylamino)-α-[(diphenylacetyl)amino]-benzeneacetamidehydrochloride a) (R,S)-N-[[4-(aminocarbonylaminomethyl)phenyl] methyl]-α-[(diphenylacetyl)amino]-3-nitrobenzeneacetamide Prepared analogously to Example 1b) from (R,S)-α-[(diphenylacetyl)amino]-3-nitrobenzeneacetic acid and 4-(aminocarbonylaminomethyl)benzenemethanamine in a yield of 65% of theory. Lemon-yellow crystals, m.p. 226–228° C.

IR (KBr):
1645.2 (broad, amide-CO),
1529.5 (amide-II, aromatic NO$_2$),
1350.1 (NO$_2$) cm$^{-1}$ b) (R,S)-3-amino-N-[[4-(aminocarbonylaminomethyl) phenyl]methyl]-α-[(diphenylacetyl)amino]-benzeneacetamide Prepared analogously to Example 1c), but using dimethylformamide as solvent and 10% palladium on activated charcoal as catalyst, from (R,S)-N-[[4-(aminocarbonylaminomethyl)phenyl]methyl]-α-[(diphenylacetyl amino]-3-nitrobenzeneacetamide in a yield of 64% of theory. Colourless crystals, m.p. 208–213° C.

IR (KBr): 1643.3 (broad, amide-CO) cm$^{-1}$
ESI-MS:
(M+H)$^+$=522
(M+Na)$^+$=544
(M+K)$^+$=560
(M+NH$_4$)$^+$=539 c) (R,S)-N-[[4-(aminocarbonylaminomethyl)phenyl]methyl]-3-(aminoiminomethylamino)-α-[(diphenylacetyl)amino]-benzeneacetamide-hydrochloride Prepared analogously to Example 1d) from (R,S)-3-amino-N-[[4-(aminocarbonylaminomethyl)phenyl]methyl]-α-[(diphenylacetyl)amino]-benzeneacetamide and cyanamide in a yield of 11% of theory. Colourless, amorphous substance, R$_f$ 0.57.
IR (KBr): 1637.5 (broad, amide-CO) cm$^{-1}$
ESI-MS:
(M+H)$^+$=564 (M+Na)$^+$=586

EXAMPLE 3

(R,S)-N-[[4-(aminocarbonylmethyl)phenyl]methyl]-3-(aminoiminomethylamino)-α-[(diphenylacetyl)amino]-benzeneacetamidehydrochloride a) (R,S)-N-[[4-(aminocarbonylmethyl)phenyl]methyl]-α-[(diphenylacetyl)amino]-3-nitrobenzeneacetamide Prepared analogously to Example 1b) from (R,S)-α-[(diphenylacetyl)amino]-3-nitrobenzeneacetic acid and 4-(aminocarbonylmethyl)benzenemethanamine in a yield of 72% of theory. Yellow crystals, m.p. 193–196° C. (D.).

IR (KBr):
1656.8 (broad), 1641.3 (amide-CO),
1531.4 (amide-II, aromatic NO$_2$),
1350.1 (NO$_2$) cm$^{-1}$ b) (R,S)-3-amino-N-[[4-(aminocarbonylmethyl)phenyl]methyl]-α-[(diphenylacetyl)amino]-benzeneacetamide Prepared analogously to Example 2b) from (R,S)-N-[[4-(amino-carbonylmethyl)phenyl]methyl]-α-[(diphenylacetyl)amino]-3-nitrobenzeneacetamide in a yield of 74% of theory. Colourless crystals, m.p. 235–237° C. (D.).

IR (KBr): 1645.2 (broad, amide-CO) cm$^{-1}$
MS: M$^+$=506 c) R,S)-N-[[4-(aminocarbonylmethyl)phenyl]methyl]-3-(aminoiminomethylamino)-α-[(diphenylacetyl)amino]-benzeneacetamide-hydrochloride Prepared analogously to Example 1d) from (R,S)-3-amino-N-[[4-(aminocarbonylmethyl)phenyl]methyl]-α-[(diphenylacetyl)amino]-benzeneacetamide and cyanamide in a yield of 73% of theory. Colourless, amorphous substance, R$_f$ 0.55.
IR (KBr): 1658.7 (broad, amide-CO) cm$^{-1}$
ESI-MS:
(M+H)$^+$=549
(M+Na)$^+$=571
(M+K)$^+$=587

EXAMPLE 4 trans-(R,S)-3-[[4-(Dimethylaminomethyl)cyclohexylmethyl]aminoiminomethylamino]-α-[(diphenylacetyl)amino]-N-methyl-N-(phenylmethyl)-benzeneacetamide-hydroiodide a) (R,S)-α-[(diphenylacetyl)amino]-N-methyl-3-nitro-N-(phenylmethyl)-benzeneacetamide Prepared analogously to Example 1b) from (R,S)-α-[(diphenylacetyl)amino]-3-nitrobenzeneacetic acid and N-methyl-benzenemethanamine in a yield of 43% of theory. Yellow crystals, m.p. 137–139° C.

IR (KBr):
1641.3 (broad, amide-CO),
1527.5 (amide-II, aromatic NO$_2$),
1346.2 (NO$_2$) cm$^{-1}$ b) (R,S)-3-amino-α-[(diphenylacetyl)amino]-N-methyl-N-(phenylmethyl)-benzeneacetamide Prepared analogously to Example 2b) from (R,S)-α-[(diphenyl-acetyl)amino]-N-methyl-3-nitro-N-(phenylmethyl)-benzene-acetamide in a yield of 99% of theory. Colourless, highly viscous substance.

IR (KBr): 1643.3 (broad, amide-CO) cm$^{-1}$ c) (R,S)-3-[[(Benzoylamino)thiocarbonyl]amino]-α-[(diphenylacetyl)amino]-N-methyl-N-(phenylmethyl)benzeneacetamide The solution of 0.82 g (10.77 mmol) of ammonium rhodanide in 140 ml of acetone was mixed with 1.51 g (10.74 mmol) of benzoylchloride and refluxed for 30 minutes. After the addition of 5.0 g (10.79 mmol) of (R,S)-3-amino-α-[(diphenylacetyl)amino]-N-methyl-N-(phenylmethyl)-benzeneacetamide the mixture was refluxed for a further 2 hours. The cooled reaction mixture was stirred into 900 ml of ice water and the precipitated oil was taken up in dichloromethane. The dichloromethane solution was dried over sodium sulphate and freed from solvent. The product obtained in a yield of 95% of theory was used in the following step without further purification.

IR (KBr): 1643.3 (broad, amide-CO) cm$^{-1}$
ESI-MS:
(M+H)$^+$=627
(M+Na)$^+$=649
(M+K)$^+$=665 d) (R,S)-3-[(aminothiocarbonyl)amino]-α-[(diphenylacetyl)amino]-N-methyl-N-(phenylmethyl)-benzeneacetamide The mixture of 6.4 g (10.22 mmol) of (R,S)-3-[[(benzoylamino)thiocarbonyl]amino]-α-[(diphenylacetyl)amino]-N-methyl-N-(phenylmethyl)-benzeneacetamide, 25.4 ml of (25.4 mmol) of 1N sodium hydroxide solution and 340 ml of ethanol was stirred for 7 hours at ambient temperature. The ethanol was distilled off in vacuo, the residue taken up in 300 ml of water and intensively stirred. The crystalline precipitate obtained was suction filtered and dried in vacuo. Pale yellow crystals, m.p. 112–115° C. Yield: 4.5 g (84% of theory).

IR (KBr): 1643.3 (broad, amide-CO) cm$^{-1}$
ESI-MS:
(M+H)$^+$=523.1
(M+Na)$^+$=545.1
(2M+Na)$^+$=1067.4 e) (R,S)-3-[(aminothiocarbonyl)amino]-α-[(diphenylacetyl)amino]-N-methyl-N-(phenylmethyl)-benzeneacetamidemethoiodide The mixture of 4.5 g (8.615 mmol) of (R,S)-3-[(aminothio-carbonyl)amino]-α-[(diphenylacetyl)amino]-N-methyl-N-(phenylmethyl)-benzeneacetamide, 86 ml of ethanol and 4.3 ml of (69 mmol) of methyliodide was stirred for 2 hours at ambient temperature and then for 2 hours at a reaction temperature of 40° C. The solvent and excess reagent were distilled off, lastly in vacuo, the residue was thoroughly stirred with diisopropylether, the yellowish crystalline product precipitated was suction filtered and dried in vacuo.

Yield: 5.4 g (94% of theory).
IR (KBr): 1633.6 (broad, amide-CO) cm$^{-1}$

ESI-MS: (M+H)$^+$=537
(M+Na)$^+$=559 f) trans-(R,S)-3-[[4-(Dimethylaminomethyl)cyclohexylmethyl]-aminoiminomethylamino]-α-[(diphenylacetyl)-amino]-N-methyl-N-(phenylmethyl)-benzeneacetamide-hydroiodide The mixture of 1.62 g (2.44 mmol) of (R,S)-3-[(aminothio-carbonyl)amino]-α-[(diphenylacetyl)amino]-N-methyl-N-(phenylmethyl)-benzeneacetamide-methoiodide, 0.425 g (2.50 mmol) of trans-4-(dimethylaminomethyl)-cyclohexane-methanamine, 30 ml of ethanol and 0.69 ml of triethylamine was refluxed for 16 hours. The residue remaining after elimination of the solvent was purified by column chromatography on silica gel (32–64 μm) using dichloromethane/methanol/cyclohexane/conc. aqueous ammonia=68/15/15/2. 0.6 g of a colourless, amorphous substance were obtained, R$_f$ 0.24.

IR (KBr): 1643.3 (broad, amide-CO) cm$^{-1}$
ESI-MS: (M+H)$^+$=659
(M+2H)$^{++}$=330

EXAMPLE 5

(R,S)-α-[(diphenylacetyl)amino]-N-methyl-3-(phenylaminoiminomethylamino)-N-(phenylmethyl)-benzeneacetamide Prepared analogously to Example 4f), but using n-propanol as solvent, from (R,S)-3-[(aminothiocarbonyl)-amino]-α-[(diphenylacetyl)amino]-N-methyl-N-(phenylmethyl)-benzeneacetamide-methoiodide and aniline in a yield of 23% of theory. Colourless, amorphous substance, R$_f$ 0.83.

IR (KBr): 1645.2 (broad, amide-CO) cm$^{-1}$
ESI-MS:
(M+H)$^+$=582
(M+Na)$^+$=604
(M+K)$^+$=620

EXAMPLE 6

(R,S)-3-(aminoiminomethylamino)-α-[(diphenylacetyl)amino]-N-methyl-N-(phenylmethyl)-benzeneacetamide-hydroiodide Prepared analogously to Example 4f), but using a bomb tube as the reaction vessel, from (R,S)-3-[(aminothiocarbonyl)amino]-α-[(diphenylacetyl)amino]-N-methyl-N-(phenyl-methyl)-benzeneacetamide-methoiodide and ammonia in a yield of 13% of theory. Colourless, amorphous substance, R$_f$ 0.75.

IR (KBr): 1645.2 (broad, amide-CO) cm$^{-1}$
ESI-MS: (M+H)$^+$=506

EXAMPLE 7

(R,S)-α-[(diphenylacetyl)amino]-N-methyl-3-(methylaminoiminomethylamino)-N-(phenylmethyl)-benzeneacetamide Prepared analogously to Example 6 from (R,S)-3-[(aminothiocarbonyl)amino]-α-[(diphenylacetyl)amino]-N-methyl-N-(phenyl-methyl)-benzeneacetamide-methoiodide and methylamine in a yield of 16% of theory. Colourless, amorphous substance, R$_f$ 0.71.
IR (KBr): 1641.3 (broad, amide-CO) cm$^{-1}$
ESI-MS: (M+H)$^+$=520

EXAMPLE 8 trans-(R,S)-N-[[4-(aminocarbonylaminomethyl)phenyl]methyl]-3-[[4-(dimethylaminomethyl)cyclohexylmethyl]aminoiminomethylamino]-α-[(diphenylacetyl)amino]-benzeneacetamide-hydroiodide a) (R,S)-N-[[4-(aminocarbonylaminomethyl)phenyl]methyl]-α-[(diphenylacetyl)amino]-3-nitrobenzeneacetamide Prepared analogously to Example 1b) from (R,S)-α-[(diphenyl-acetyl)amino]-3-nitrobenzeneacetic acid and 4-(aminocar-bonylaminomethyl)-benzenemethanamine in a yield of 94% of theory. Yellow crystals, m.p. 220–225° C.

IR (KBr):
1645.2 (broad, amide-CO),
1529.5 (amide-II, aromatic NO$_2$),
1350.1 (NO$_2$) cm$^{-1}$ b) (R,S)-3-amino-N-[[4-(aminocarbonylaminomethyl)phenyl]methyl]-α-[(diphenylacetyl)amino]-benzeneacetamide Prepared analogously to Example 2b) from (R,S)-N-[[4-(aminocarbonylaminomethyl)phenyl]methyl]-α-[(diphenylacetyl)amino]-3-nitrobenzeneacetamide in a yield of 98% of theory. Colourless crystals, m.p. 207–209° C.

IR (KBr): 1641.3 (broad, amide-CO) cm$^{-1}$ c) (R,S)-N-[[4-(aminocarbonylaminomethyl)phenyl]methyl]-3-[[(benzoylamino)thiocarbonyl]amino]-α-[(diphenylacetyl)amino]-benzeneacetamide Prepared analogously to Example 4c) from (R,S)-3-amino-N-[[4-(aminocarbonylaminomethyl)phenyl]methyl]-α-[(diphenylacetyl)amino]-benzeneacetamide, ammonium rhodanide and benzoylchloride in a yield of 78% of theory. Colourless, amorphous substance.

IR (KBr): 1635.5 (broad, amide-CO) cm$^{-1}$
ESI-MS: (M+H)$^+$=685
(M+Na)$^+$=707
(M−H)$^-$=683 d) (R,S)-N-[[4-(aminocarbonylaminomethyl)phenyl]methyl]-3-[(aminothiocarbonyl)amino]-α-[(diphenylacetyl)amino]benzeneacetamide Prepared analogously to Example 4d) from (R,S)-N-[[4-(amino-carbonylaminomethyl)phenyl]methyl]-3-[[(benzoylamino)-thiocarbonyl]amino]-α-[(diphenylacetyl)amino]benzene-acetamide by saponification with 1N sodium hydroxide solution in a yield of 92% of theory. Colourless crystals, m.p. 151–153° C.

IR (KBr): 1637.5 (broad, amide-CO) cm$^{-1}$
ESI-MS:
(M+H)$^+$=581
(M+Na)$^+$=603
(M−H)$^-$=579 e) (R,S)-N-[[4-(aminocarbonylaminomethyl)phenyl]methyl]-3-[(aminothiocarbonyl)amino]-α-[(diphenylacetyl)amino]benzeneacetamide-methoiodide Prepared analogously to Example 4e) from (R,S)-N-[[4-(amino-carbonylaminomethyl)phenyl]methyl]-3-[(aminothiocar-bonyl)amino]-α-[(diphenylacetyl)amino]benzeneacetamide and methyliodide in a yield of 87% of theory. Colourless crystals.

IR (KBr): 1635.5 (broad, amide-CO) cm$^{-1}$
ESI-MS:
(M+H)$^+$=595
(M+Na)$^+$=617 f) trans-(R,S)-N-[[4-(aminocarbonylaminomethyl)phenyl]methyl]-3-[[4-(dimethylaminomethyl)cyclohexylmethyl]aminoiminomethylamino]-α-[(diphenylacetyl)amino]-benzeneacetamide-hydroiodide Prepared analogously to Example 4f) from (R,S)-N-[[4-(amino-carbonylaminomethyl)phenyl]methyl]-3-[(aminothiocar-bonyl)amino]-α-[(diphenylacetyl)amino]benzeneacetamide-methoiodide and trans-4-(dimethylaminomethyl)-cyclohexanemethanamine in a yield of 35% of theory. Colourless, amorphous substance, $R_f$ 0.18.

IR (KBr): 1652.9 (broad, amide-CO) cm$^{-1}$
ESI-MS:
(M+H)$^+$=717
(M+Na)$^+$=739
(M+2H)$^{++}$=359

EXAMPLE 9

(R,S)-N-[[4-(aminocarbonylaminomethyl)phenyl]methyl]-α-[(diphenylacetyl)amino]-3-[(methylaminocarbonyl)aminoimino-methylamino]benzeneacetamide The mixture of 2.5 g (4.80 mmol) of (R,S)-3-amino-N-[[4-(amino-carbonylaminomethyl)phenyl]methyl]-α-[(diphenylacetyl)amino]-benzeneacetamide, 18 ml of isopropanol, 20 ml of dimethylformamide and 3 ml of acetic acid was heated to 80° C. for 72 hours, whilst 0.4 g (3.48 mmol) of O-Methyl-N-(methylaminocarbonyl)-isourea were added to the mixture are the beginning and after 12, 24, 36, 48 and 60 hours. The solvent was eliminated in vacuo, the residue was taken up in 50 ml of dichloromethane, stirred for 30 minutes at ambient temperature and the precipitate obtained was suction filtered. The filtrate was once more evaporated down in vacuo, the residue was purified by column chromatography on silica gel (Baker, 30–60 μm) using dichloromethane/ethyl acetate/methanol/cyclohexane/conc. aqueous ammonia 59/25/7,5/7,5/1 (v/v/v/v) as eluant. Working up the appropriate eluates yielded 60 mg (2% of theory) of a colourless, crystalline substance, $R_f$ 0.66.

IR (KBr): 1652.9 (broad, amide-CO) cm$^{-1}$
ESI-MS:
(M+H)$^+$=621
(M+Na)$^+$=643
(M+K)$^+$=659

EXAMPLE 10

(R,S)-N-[[4-(aminocarbonylaminomethyl)phenyl]methyl]-α-[(diphenylacetyl)amino]-3-[(4-methoxyphenyl)aminoimino-methylamino]-benzeneacetamide-hydroiodide Prepared analogously to Example 4f), but using n-propanol as solvent, from (R,S)-N-[[4-(aminocarbonylaminomethyl)phenyl]methyl]-3-[(aminothiocarbonyl)amino]-α-[(diphenylacetyl)amino]-benzeneacetamide-methoiodide and p-anisidine in a yield of 8% of theory. Colourless, amorphous substance, $R_f$ 0.67.

IR (KBr) : 1645.2 (broad, amide-CO) cm$^{-1}$
ESI-MS:
(M+H)$^+$=670
(M+Na)$^+$=692

EXAMPLE 11

(R,S)-α-[(diphenylacetyl)amino]-3-[(4-methoxyphenyl)aminoiminomethylamino]-N-(phenylmethyl)-benzeneacetamide a) (R,S)-α-[(diphenylacetyl)amino]-3-nitro-N-(phenylmethyl)-benzeneacetamide Prepared analogously to Example 1b) from (R,S)-α-[(diphenylacetyl) amino]-3-nitrobenzeneacetic acid and benzenemethanamine in a yield of 47% of theory. Yellow crystals.

IR (KBr):
1635.5 (broad, amide-CO),
1531.4 (amide-II, aromatic NO$_2$),
1350.1 (NO$_2$) cm$^{-1}$ b) (R,S)-3-amino-α-[(diphenylacetyl)amino]-N-(phenyl-methyl)-benzeneacetamide Prepared analogously to Example 2b) from (R,S)-α-[(diphenyl-acetyl)amino]-3-nitro-N-(phenylmethyl)-benzeneacetamide in a yield of 80% of theory.
Colourless crystals.

IR (KBr): 1641.3 (broad, amide-CO) cm$^{-1}$ c) (R,S)-3-[[(benzoylamino)thiocarbonyl]amino]-α-[(diphenylacetyl)amino]-N-(phenylmethyl)-benzeneacetamide Prepared analogously to Example 4c) from (R,S)-3-amino-α-[(diphenylacetyl)amino]-N-(phenylmethyl)-benzeneacetamide, ammonium rhodanide and benzoylchloride in a yield of 97% of theory. Colourless crystals.

IR (KBr): 1641.3 (broad, amide-CO) cm$^{-1}$
ESI-MS:
(M+H)$^+$=613
(M+Na)$^+$=635
(M−H)$^-$=611 d) (R,S)-3-[(aminothiocarbonyl)amino]-α-[(diphenyl-acetyl)amino]-N-(phenylmethyl)-benzeneacetamide Prepared analogously to Example 4d) from (R,S)-3-[[(benzoyl-amino)thiocarbonyl]amino]-α-[(diphenylacetyl)amino]-N-(phenylmethyl)-benzeneacetamide by saponification with 1N sodium hydroxide solution in a yield of 99% of theory.
Colourless, amorphous substance.

IR (KBr): 1637.5 (broad, amide-CO) cm$^{-1}$
ESI-MS:
(M−H)$^-$=507
(M+Na)$^+$=531 e) (R,S)-3-[(aminothiocarbonyl)amino]-α-[(diphenylacetyl)-amino]-N-(phenylmethyl)-benzeneacetamide-methoiodide Prepared analogously to Example 4e) from (R,S)-3-[(amino-thiocarbonyl)amino]-α-[(diphenylacetyl)amino]-N-(phenyl-methyl)-benzeneacetamide and methyliodide in a yield of 99% of theory. Colourless, amorphous substance.

IR (KBr): 1645.2 (broad, amide-CO) cm$^{-1}$
ESI-MS:
(M+H)$^+$=523
(M+Na)$^+$=545 f) (R,S)-α-[(diphenylacetyl)amino]-3-[(4-methoxyphenyl)-aminoiminomethylamino]-N-(phenylmethyl)-benzeneacetamide Prepared analogously to Example 10 from (R,S)-3-[(aminothiocarbonyl)amino]-α-[(diphenylacetyl)amino]-N-(phenylmethyl)-benzeneacetamide-methoiodide and p-anisidine in a yield of 22% of theory. Colourless, crystalline substance, m.p. 126–132° C. and $R_f$ 0.84.

IR (KBr): 1649.0 (broad, amide-CO) cm$^{-1}$
ESI-MS:
(M+H)$^+$=598
(M+Na)$^+$=620
(M+K)$^+$=636

EXAMPLE 12

(R,S)-N-[[4-(aminocarbonylaminomethyl)phenyl]methyl]-α-[(diphenylacetyl)amino]-3-[[imino[N-methyl-N-(phenylmethyl)amino]methyl]amino]-benzeneacetamide Prepared analogously to Example 10 from (R,S)-N-[[4-(aminocarbonylaminomethyl)phenyl]methyl]-3-

[(aminothiocarbonyl)amino]-α-[(diphenylacetyl)amino]-benzeneacetamide-methoiodide and N-methylbenzenemethanamine in a yield of 21% of theory. Colourless, amorphous substance, $R_f$ 0.56.
IR (KBr): 1649.0 (broad, amide-CO) cm$^{-1}$
ESI-MS:
(M+H)$^+$=668
(M+Na)$^+$=690

EXAMPLE 13

(R,S)-N-[[4-(aminocarbonylaminomethyl)phenyl]methyl]-α-[(diphenylacetyl)amino]-3-(methylaminoiminomethylamino)-benzeneacetamide-acetate Prepared analogously to Example 10), but using a steel bomb as the reaction vessel, from (R,S)-N-[[4-(aminocarbonylaminomethyl)phenyl]methyl]-3-[(aminothiocarbonyl)amino]-α-[(diphenylacetyl)amino]-benzeneacetamide-methoiodide and methylamine in a yield of 63% of theory. Colourless crystals, $R_f$ 0.47.
IR (KBr): 1639.4 (broad, amide-CO) cm$^{-1}$
ESI-MS:
(M+H)$^+$=578
(M+Na)$^+$=600

EXAMPLE 14

(R,S)-α-[(diphenylacetyl)amino]-3-[(4-methoxyphenyl)aminoiminomethylamino]-N-[[(4-phenylmethoxy)phenyl]methyl]benzeneacetamide a) (R,S)-α-[(diphenylacetyl)amino]-3-nitro-N-[[(4-phenylmethoxy)phenyl]methyl]-benzeneacetamide Prepared analogously to Example 1b) from (R,S)-α-[(diphenyl-acetyl)amino]-3-nitrobenzeneacetic acid and 4-(phenyl-methoxy)-benzenemethanamine in a yield of 57% of theory. Yellow crystals, m.p. 185–190° C.

IR (KBr):
1641.3 (broad, amide-CO),
1531.4 (amide-II, aromatic NO$_2$)
1352.0 (NO$_2$) cm$^{-1}$ b) (R,S)-3-amino-α-[(diphenylacetyl)amino]-N-[[(4-phenylmethoxy)phenyl]methyl]-benzeneacetamide Prepared analogously to Example 1c), but using dimethylformamide as solvent, from (R,S)-α-[(diphenylacetyl)amino]-3-nitro-N-[[(4-phenylmethoxy)-phenyl]methyl]-benzeneacetamide in a yield of 73% of theory. Colourless crystals.

IR (KBr): 1635.5 (broad, amide-CO) cm$^{-1}$ c) (R,S)-3-[[(benzoylamino)thiocarbonyl]amino]-α-[(diphenylacetyl)amino]-N-[[(4-phenylmethoxy)phenyl]methyl]benzeneacetamide Prepared analogously to Example 4c) from (R,S)-3-amino-α-[(diphenylacetyl)amino]-N-[[(4-phenylmethoxy)phenyl]methyl]-benzeneacetamide, ammonium rhodanide and benzoylchloride in a yield of 99% of theory. Colourless crystals.

IR (KBr): 1637.5 (broad, amide-CO) cm$^{-1}$ d) (R,S)-3-[(aminothiocarbonyl)amino]-α-[(diphenyl-acetyl)-amino]-N-[[(4-phenylmethoxy)phenyl]methyl]-benzeneacetamide Prepared analogously to Example 4d) from (R,S)-3-[[(benzoyl-amino)thiocarbonyl]amino]-α-[(diphenylacetyl)amino]-N-[[(4-phenylmethoxy)phenyl]methyl]-benzeneacetamide by saponification with 1N sodium hydroxide solution in a yield of 81% of theory. Colourless crystals.

IR (KBr): 1637.5 (broad, amide-CO) cm$^{-1}$
ESI-MS:
(M–H)$^-$=613
(M+Na)$^+$=637 e) (R,S)-3-[(aminothiocarbonyl)amino]-α-[(diphenylacetyl)-amino]-N-[[(4-phenylmethoxy)phenyl]methyl]-benzeneacetamide-methoiodide Prepared analogously to Example 4e) from (R,S)-3-[(aminothio-carbonyl)amino]-α-[(diphenylacetyl)amino]-N-[[(4-phenyl-methoxy)phenyl]methyl]-benzeneacetamide and methyliodide in a yield of 98% of theory. Colourless, amorphous substance.

IR (KBr): 1633.6 (broad, amide-CO) cm$^{-1}$
ESI-MS:
(M+H)$^+$=629
(M+Na)$^+$=651 f) (R,S)-α-[(diphenylacetyl)amino]-3-[(4-methoxyphenyl)-aminoiminomethylamino]-N-[[(4-phenylmethoxy)phenyl]-methyl]-benzeneacetamide Prepared analogously to Example 10 from (R,S)-3-[(aminothio-carbonyl)amino]-α-[(diphenylacetyl)amino]-N-[[(4-phenyl-methoxy)phenyl]methyl]-benzeneacetamidemethoiodide and p-anisidine in a yield of 27% of theory. Colourless, crystalline substance, m.p. 196–198° C. and $R_f$ 0.90.

IR (KBr): 1639.4 (broad, amide-CO) cm$^{-1}$
ESI-MS:
(M+H)$^+$=704
(M+Na)$^+$=726

EXAMPLE 15

(R,S)-3-(aminoiminomethylamino)-α-[(diphenylacetyl)amino]-N-[[(4-phenylmethoxy)phenyl]methyl]-benzeneacetamide Prepared analogously to Example 4f) from (R,S)-3-[(aminothiocarbonyl)amino]-α-[(diphenylacetyl)amino]-N-[[(4-phenylmethoxy)phenyl]methyl]-benzeneacetamide-methoiodide and ammonia in a yield of 13% of theory. Colourless crystals, m.p. 198–200° C. and $R_f$ 0.79.

IR (KBr): 1645.2 (broad, amide-CO) cm$^{-1}$
ESI-MS:
(M+H)$^+$=598
(M+Na)$^+$=620

EXAMPLE 16

(R,S)-3-(aminoiminomethylamino)-α-[(diphenylacetyl)amino]-N-methyl-N-[[(4-phenylmethoxy)phenyl]methyl]-benzeneacetamide a) (R,S)-α-[(diphenylacetyl)amino]-3-nitro-N-methyl-N-[[(4-phenylmethoxy)phenyl]methyl]-benzeneacetamide Prepared analogously to Example 1b) from (R,S)-α-[(diphenyl-acetyl)amino]-3-nitrobenzeneacetic acid and N-Methyl-4-(phenylmethoxy)-benzenemethanamine in a yield of 56% of theory. Yellow crystals.

IR (KBr):
1643.3 (broad, amide-CO),
1510.2 (amide-II, aromatic NO$_2$),
1350.1 (NO$_2$) cm$^{-1}$ b) (R,S)-3-amino-α-[(diphenylacetyl)amino]-N-methyl-N-[[(4-phenylmethoxy)phenyl]methyl]-benzeneacetamide Prepared analogously to Example 1c), but using methanol as solvent, from (R,S)-α-[(diphenyl-acetyl)amino]-3-nitro- N-methyl-N-[[(4-phenylmethoxy)-phenyl]methyl]-benzeneacetamide in a yield of 71% of theory.

Colourless crystals, m.p. 141–143° C.

IR (KBr): 1643.3 (broad, amide-CO) cm$^{-1}$ c) (R,S)-3-[[(benzoylamino)thiocarbonyl]amino]-α-[(diphenylacetyl)amino]-N-methyl-N-[[(4-phenylmethoxy)phenyl]methyl]-benzeneacetamide Prepared analogously to Example 4c) from (R,S)-3-amino-α-[(diphenylacetyl)amino]-N-methyl-N-[[(4-phenylmethoxy)phenyl]methyl]-benzeneacetamide, ammonium rhodanide and benzoylchloride in a yield of 98% of theory.

Colourless crystals.

IR (KBr): 1643.3 (broad, amide-CO) cm$^{-1}$
ESI-MS:
(M–H)$^+$=733
(M+Na)$^+$=755
(M+NH$_4$)$^+$=750 d) (R,S)-3-[(aminothiocarbonyl)amino]-α-[(diphenylacetyl)amino]-N-methyl-N-[[(4-phenylmethoxy)phenyl]methyl]benzeneacetamide Prepared analogously to Example 4d) from (R,S)-3-[[(benzoyl-amino)thiocarbonyl]amino]-α-[(diphenylacetyl)amino]-N-[[(4-phenylmethoxy)phenyl]methyl]-benzeneacetamide by saponification with 1N sodium hydroxide solution in a yield of 99% of theory. Colourless crystals.

IR (KBr): 1643.3 (broad, amide-CO) cm$^{-1}$
ESI-MS:
(M+H)$^+$=629
(M+NH$_4$)$^+$=646
(M+Na)$^+$=651 e) (R,S)-3-[(aminothiocarbonyl)amino]-α-[(diphenylacetyl)-amino]-N-methyl-N-[[(4-phenylmethoxy)phenyl]-methyl]-benzeneacetamide-methoiodide Prepared analogously to Example 4e) from (R,S)-3-[(amino-thiocarbonyl)amino]-α-[(diphenylacetyl)amino]-N-methyl-N-[[(4-phenylmethoxy)phenyl]methyl]-benzeneacetamide and methyliodide in a yield of 89% of theory. Colourless, amorphous substance.

IR (KBr): 1631.7 (broad, amide-CO) cm$^{-1}$
ESI-MS:
(M+H)$^+$=643
(M+Na)$^+$=665 f) (R,S)-3-(aminoiminomethylamino)-α-[(diphenylacetyl)amino]-N-methyl-N-[[(4-phenylmethoxy)phenyl]methyl]benzeneacetamide Prepared analogously to Example 6 from (R,S)-3-[(aminothio-carbonyl)amino]-α-[(diphenylacetyl)amino]-N-methyl-N-[[(4-phenylmethoxy)phenyl]methyl]benzeneacetamide-methoiodide and ammonia in a yield of 17% of theory. Colourless, crystalline substance, R$_f$ 0.80.

IR (KBr): 1645.2 (broad, amide-CO) cm$^{-1}$
ESI-MS:
(M+H)$^+$=612
(M+Na)$^+$=634

EXAMPLE 17

(R,S)-N-[[4-(aminocarbonylaminomethyl)phenyl]methyl]-α-[(diphenylacetyl)amino]-N-methyl-3-(methylamino-iminomethylamino)benzeneacetamide-hydrochloride a) (R,S)-N-[[4-(aminocarbonylaminomethyl)phenyl]methyl]-α-[(diphenylacetyl)amino]-3-nitro-N-methylbenzeneacetamide Prepared analogously to Example 1b), but using pure dimethylformamide as solvent, from (R,S)-α-[(diphenylacetyl)amino]-3-nitrobenzeneacetic acid and 4-(aminocarbonylaminomethyl)-N-methyl-benzenemethanamine in a yield of 71% of theory. Yellow crystals.

IR (KBr): 1652.9 (broad, amide-CO), b) (R,S)-3-amino-N-[[4-(aminocarbonylaminomethyl)phenyl]methyl]-α-[(diphenylacetyl)amino]-N-methyl-benzeneacetamide Prepared analogously to Example 1c), but using methanol as solvent, from (R,S)-N-[[4-(aminocarbonylaminomethyl)phenyl]methyl]-α-[(diphenylacetyl)-amino]-3-nitro-N-methyl-benzeneacetamide in a yield of 42% of theory.

Colourless, amorphous substance.

IR (KBr): 1643.3 (broad, amide-CO) cm$^{-1}$ c) (R,S)-N-[[4-(aminocarbonylaminomethyl)phenyl]methyl]-3-[[(benzoylamino)thiocarbonyl]amino]-α-[(diphenyl-acetyl)amino]-N-methyl-benzeneacetamide Prepared analogously to Example 4c) from (R,S)-3-amino-N-[[4-(aminocarbonylaminomethyl)phenyl]methyl]-α-[(diphenylacetyl)amino]-N-methyl-benzeneacetamide, ammonium rhodanide and benzoylchloride in a yield of 92% of theory. Colourless crystals.

IR (KBr): 1647.1 (broad, amide-CO) cm$^{-1}$
ESI-MS:
(M+H)$^+$=699
(M–H)$^-$=697
(M+Na)$^+$=721
(M+NH$_4$)$^+$=716 d) (R,S)-N-[[4-(aminocarbonylaminomethyl)phenyl]methyl]-3-[(aminothiocarbonyl)amino]-α-[(diphenylacetyl)amino]-N-methyl-benzeneacetamide Prepared analogously to Example 4d) from (R,S)-N-[[4-(amino-carbonylaminomethyl)phenyl]methyl]-3-[[(benzoylamino)-thiocarbonyl]amino]-α-[(diphenylacetyl)amino]-N-methyl-benzeneacetamide by saponification with 1N sodium hydroxide solution in a yield of 94% of theory. Colourless crystals.

IR (KBr): 1645.2 (broad, amide-CO) cm$^{-1}$
ESI-MS:
(M+H)$^+$=595
(M+Na)$^+$=617
(M+K)$^+$=633 e) (R,S)-N-[[4-(aminocarbonylaminomethyl)phenyl]methyl]-3-[(aminothiocarbonyl)amino]-α-[(diphenylacetyl)amino]-N-methyl-benzeneacetamide-methoiodide Prepared analogously to Example 4e) from (R,S)-N-[[4-(amino-carbonylaminomethyl)phenyl]methyl]-3-[(aminothiocarbonyl)amino]-α-[(diphenylacetyl)amino]-N-methyl-benzeneacetamide and methyliodide in a yield of 95% of theory. Colourless, crystalline substance.

IR (KBr): 1639.4 (broad, amide-CO) cm$^{-1}$
ESI-MS:
(M+H)$^+$=609
(M+Na)$^+$=631
(M+K)$^+$=647 f) (R,S)-N-[[4-(aminocarbonylaminomethyl)phenyl]methyl]-α-[(diphenylacetyl)amino]-N-methyl-3-(methylamino-iminomethylamino)-benzeneacetamide-hydrochloride Prepared analogously to Example 13 from (R,S)-N-[[4-(amino-carbonylaminomethyl)phenyl]methyl]-3-[(aminothiocarbonyl)amino]-α-[(diphenylacetyl)amino]-N-methyl-benzeneacetamide-methoiodide and methylamine in a yield of 68% of theory. Colourless, crystalline substance, R$_f$ 0.45.

IR (KBr): 1645.2 (broad, amide-CO) cm$^{-1}$
ESI-MS: (M+H)$^+$=592

We claim:
1. A compound of the formula

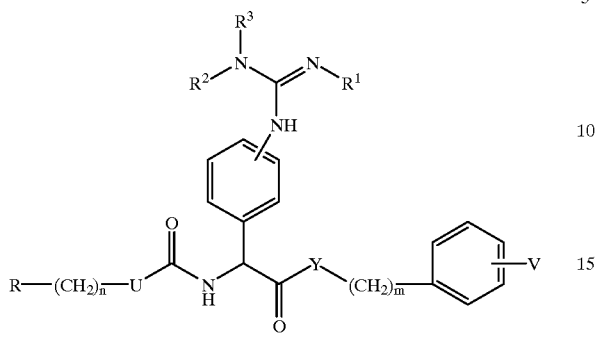

(I)

wherein
R denotes a phenyl, 1-naphthyl or 2-naphthyl group, a 5-membered heteroaromatic ring linked via a carbon atom and containing a nitrogen, oxygen or sulphur atom or a nitrogen atom and an oxygen, a sulphur or a further nitrogen atom, whilst a nitrogen atom of an imino group may be substituted by an alkyl, alkoxycarbonylalkyl, carboxyalkyl, dialkylaminoalkyl, aminocarbonyl, alkylaminocarbonyl, dialkylaminocarbonyl or alkoxycarbonyl group, or a 6-membered heteroaromatic ring linked via a carbon atom and containing 1, 2 or 3 nitrogen atoms, whilst a 1,4-butadienylene group may be attached both to the 5-membered and to the 6-membered heteroaromatic rings via two adjacent carbon atoms and the bicyclic heteroaromatic rings thus formed may also be bound via a carbon atom of the 1,4-butadienylene group and the groups mentioned for R hereinbefore, including the mono- and bicyclic heteroaromatic rings in their carbon skeleton, may additionally be mono-, di- or at most trisubstituted by fluorine, chlorine or bromine atoms, by alkyl groups, cycloalkyl groups with 3 to 8 carbon atoms, alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different and the abovementioned benzoyl, benzoylamino and benzoylmethylamino groups in turn may additionally be substituted in the phenyl moiety by a fluorine, chlorine or bromine atom, an alkyl, trifluoromethyl, amino or acetylamino group, or the diphenylmethyl group, wherein
the phenyl groups independently of one another may be mono- or disubstituted by fluorine, chlorine or bromine atoms, methyl, methoxy, hydroxycarbonylmethoxy, alkoxycarbonylmethoxy, hydroxy or trifluoromethyl groups, whilst the substituents in each case may be identical or different, n denotes the numbers 0, 1 or 2,
U denotes a single bond, an oxygen atom or the —NH group,
$R^1$ denotes a hydrogen atom,
a straight-chained or branched alkyl group with 1 to 8 carbon atoms which may be terminally substituted by a cycloalkyl group with 3 to 8 carbon atoms, or denotes a cycloalkyl group with 3 to 8 carbon atoms, whilst the abovementioned groups may in turn be substituted by an alkoxycarbonyl, phenylalkoxycarbonyl, carboxy, amino, monoalkylamino, dialkylamino or dialkylaminomethyl group, a branched or unbranched alkylcarbonyl group containing 2 to 5 carbon atoms, which may be substituted in the alkyl moiety by an alkoxycarbonyl or phenylalkoxycarbonyl group, by a phenyl group or by a 5- or 6-membered heteroaromatic ring linked via a carbon atom, or a benzoyl group, wherein the phenyl moiety may also be replaced by a 5- or 6-membered heteroaromatic ring linked via a carbon atom, whilst the 5-membered heteroaromatic rings mentioned hereinbefore may contain a nitrogen, an oxygen or a sulphur atom or a nitrogen atom and an additional oxygen, sulphur or further nitrogen atom and may also be substituted by an alkyl group at a nitrogen atom, the 6-membered heteroaromatic rings may contain 1, 2 or 3 nitrogen atoms, and the phenyl groups mentioned hereinbefore may additionally be mono-, di- or at most tri-substituted, as may all the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different, the aminocarbonyl group, which may be mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, carboxyalkyl, diphenylalkyl, phenyl, cycloalkyl or cycloalkylalkyl groups with 3 to 8 carbon atoms in the ring in each case, whilst the substituents may be identical or different and the abovementioned phenyl groups may in turn, independently of one another, be mono- or disubstituted by fluorine, chlorine or bromine atoms, methyl, methoxy, hydroxycarbonylmethoxy, alkoxycarbonylmethoxy, hydroxy or trifluoromethyl groups, an alkoxycarbonyl or phenylalkoxycarbonyl group, whilst the phenyl moiety in its turn may be mono- or disubstituted by fluorine, chlorine or bromine atoms, methyl, methoxy, hydroxycarbonylmethoxy, alkoxycarbonylmethoxy, hydroxy or trifluoromethyl groups and the substituents in each case may be identical or different, a phenyl or phenylmethyl group, a hetaryl or hetarylmethyl group linked via a carbon atom, wherein hetaryl denotes a five-membered heteroaromatic ring which contains a nitrogen, oxygen or sulphur atom or a nitrogen atom and an oxygen, sulphur or further nitrogen atom, and wherein a nitrogen atom of an imino group may be substituted by an alkyl group, or a 6-membered heteroaromatic ring linked via a carbon atom, which contains 1, 2 or 3 nitrogen atoms, and wherein the phenyl group may additionally be mono-, di- or at most trisubstituted, as may hetaryl in the carbon skeleton, by fluorine, chlorine or bromine atoms, by alkyl groups, cycloalkyl groups with 3 to 8 carbon atoms, phenylalkyl, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups and the substituents may be identical or different, $R^2$ denotes a hydrogen atom, an alkyl or phenylalkyl group, which may also be mono- or disubstituted in the phenyl moiety by fluorine, chlorine or bromine atoms, alkyl, trifluoromethyl, amino or acetylamino groups, whilst the substituents may be identical or different, $R^3$ denotes a hydrogen atom or an alkyl group, Y denotes an oxygen atom or the —$NR^4$— group wherein
  $R^4$ denotes a hydrogen atom, a branched or unbranched alkyl group with 1 to 6 carbon atoms or the phenylmethyl group, m denotes the numbers 1 or 2 and V denotes a hydrogen atom, a fluorine, chlorine, bromine or iodine atom, a cyano, alkyl, hydroxy, alkoxy, phenylalkoxy, alkylcarbonyl, dialkylamino, hydroxymethyl, hydroxyethyl, hydroxypropyl, hydroxybutyl, trifluoromethyl, trifluoromethoxy or trifluoromethylthio group or the group —$(CH_2)_o$—$Y^1$—W—$Y^2$, wherein o denotes the numbers 0, 1 or 2, W denotes the —$SO_2$— group or the group >C=X wherein
  X denotes an oxygen atom or one of the divalent groups =N—$CONH_2$ or =N—CN, $Y^1$ denotes a single bond, an oxygen atom or the group —$NR^5$— wherein
  $R^5$ denotes a hydrogen atom or a straight-chained or branched alkyl group with 1 to 6 carbon atoms or
  $R^5$ together with the group $y^2$, the enclosed nitrogen atom and the enclosed group >C=X forms a saturated heterocyclic ring with 5 to 7 ring members, $Y^2$ denotes a straight-chained or branched alkyl group with 1 to 10 carbon atoms optionally substituted by a hydroxy, alkoxycarbonyl or aminocarbonyl group, a cycloalkyl group with 4 to 10 carbon atoms, a straight-chained or branched alkoxy group with 1 to 5 carbon atoms, an aminoalkyl, alkylaminoalkyl, dialkylaminoalkyl, phenylmethoxy or 2-phenylethoxy group, a phenyl or phenylalkyl group with 1 to 3 carbon atoms in the alkyl moiety optionally mono-, di- or trisubstituted in the phenyl moiety by fluorine, chlorine or bromine atoms, by methyl, trifluoromethyl, cyano, amino, hydroxy, methoxy, acetyl, acetylamino, aminocarbonyl, methylaminocarbonyl or dimethylaminocarbonyl groups, or the —$NR^6R^7$ group wherein
  $R^6$ denotes a hydrogen atom, a straight-chained or branched alkyl group with 1 to 6 carbon atoms optionally substituted by a hydroxy, carboxy, alkoxycarbonyl or dialkylamino group with the proviso that the hydroxy group is not bound in the 1-position of the alkyl group, a cycloalkyl group with 4 to 8 carbon atoms or a phenyl, phenylmethyl, 2-phenylethyl or 3-phenylpropyl group optionally mono-, di- or trisubstituted in the phenyl moiety by fluorine, chlorine or bromine atoms, by methyl, trifluoromethyl, hydroxy, methoxy, amino, acetylamino, aminocarbonyl, methylaminocarbonyl, dimethylaminocarbonyl or cyano groups, whilst the substituents may be identical or different, or an alkanoyl, benzoyl, phenylalkanoyl, alkoxycarbonyl or aminocarbonyl group and
  $R^7$ has the meanings given for $R^6$ with the exception of a phenyl, alkanoyl, benzoyl, phenylalkanoyl, alkoxycarbonyl or aminocarbonyl group or $R^6$ and $R^7$ together denote an n-alkylene group with 4 to 6 carbon atoms or $R^7$ together with the group $R^5$ of the group —$NR^5$— mentioned for $Y^1$ hereinbefore denotes an unbranched alkylene group or oxoalkylene group with 2 to 4 carbon atoms, whilst all the abovementioned alkyl, cycloalkylalkyl, alkoxy, phenoxycarbonylalkyl, phenylalkoxy, phenylalkoxycarbonyl, phenylalkoxycarbonylalkyl, phenylalkanoyl, phenylalkyl, diphenylalkyl, naphthylalkyl, alkoxycarbonylalkyl, alkoxycarbonylmethoxy, carboxyalkyl, aminoalkyl, monoalkylamino, dialkylamino, alkylaminoalkyl, dialkylaminomethyl, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties, or a tautomer, diastereomer, enantiomer or physiologically acceptable salt thereof.

2. A compound of the formula

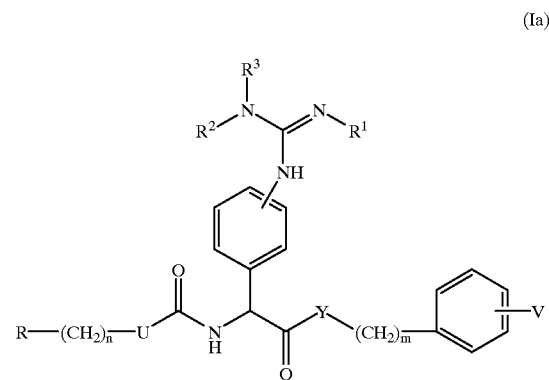

(Ia)

wherein
  R, n, U, $R^1$, $R^2$, $R^3$, V, Y and m are defined as in claim 1,
  V is bound in the 3- or 4-position of the benzene ring and denotes a hydrogen atom, a fluorine, chlorine, bromine or iodine atom, a cyano, alkyl, hydroxy, alkoxy, alkylcarbonyl, dialkylamino, hydroxymethyl, hydroxyethyl, hydroxypropyl, hydroxybutyl, trifluoromethyl, trifluoromethoxy, trifluoromethylthio group or the group —$(CH_2)_o$—$Y^1$—(CO)—W—$Y^2$ wherein
    o, $Y^1$ and $Y^2$ are defined as in claim 1,
whilst, unless otherwise specified, the alkyl, alkoxy, alkylcarbonyl and dialkylamino groups mentioned for V hereinbefore may contain 1 to 5 carbon atoms in the alkyl and alkoxy moieties,
or a tautomer, diastereomer, enantiomer or physiologically acceptable salt thereof.

3. A compound of the formula Ia according to claim 2, wherein
  R denotes a phenyl, 1-naphthyl or 2-naphthyl group, a 5-membered heteroaromatic ring linked via a carbon atom, which contains a nitrogen, oxygen or sulphur atom, whilst a nitrogen atom of an imino group may be substituted by an alkyl group, or a 6-membered heteroaromatic ring linked via a carbon atom, which contains 1 or 2 nitrogen atoms, whilst the groups mentioned for R hereinbefore, including the heteroaromatic rings in their carbon skeleton, may additionally be substituted by a fluorine, chlorine or bromine atom, by an alkyl group, by a cycloalkyl group with 3 to 6 carbon atoms, by an alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano or trifluoromethoxy group, or the diphenylmethyl group wherein the phenyl groups may be substituted independently of one another by a fluorine, chlorine or bromine atom, by a methyl, methoxy, hydroxycarbonylmethoxy, alkoxycarbonylmethoxy, hydroxy or trifluoromethyl group, n denotes the number 0 or 1, U denotes a single bond, $R^1$ denotes a hydrogen atom, a straight-chained or branched alkyl group having 1 to 5 carbon atoms which may be terminally substituted by a cycloalkyl group having 4 to 7 carbon atoms, or denotes a cycloalkyl group having 4 to 7 carbon atoms, whilst the abovementioned groups may in turn be substituted by an alkoxycarbonyl, phenylalkoxycarbonyl, carboxy, amino, monoalkylamino, dialkylamino or dialkylaminomethyl group, a branched or unbranched aliphatic acyl group containing 2 to 4 carbon atoms which may be substituted by an alkoxycarbonyl or phenylalkoxycarbonyl group or by a phenyl group optionally substituted by a fluorine, chlorine or bromine atom, by an alkyl group, a cycloalkyl group with 4 to 7 carbon atoms, or by an alkoxy, trifluoromethyl, hydroxy, amino, acetylamino or cyano group, or a benzoyl group, the aminocarbonyl group, which may be substituted at the nitrogen atom by an alkyl, phenylalkyl, (1-naphthyl) alkyl, (2-naphthyl)alkyl, alkoxycarbonylalkyl, carboxyalkyl, ω,ω-diphenylalkyl, phenyl, cycloalkyl or cycloalkylalkyl groups each with 3 to 6 carbon atoms in the ring, whilst the phenyl groups in the abovementioned groups may in turn be substituted by a fluorine, chlorine or bromine atom, or by a methyl, methoxy, hydroxy or trifluoromethyl group, an alkoxycarbonyl or phenylalkoxycarbonyl group, which may be substituted in the phenyl moiety by a fluorine, chlorine or bromine atom, by a methyl, methoxy, hydroxy or trifluoromethyl group, a phenyl group or a five-membered heteroaromatic ring bound via a carbon atom, which contains a nitrogen, oxygen or sulphur atom, whilst a nitrogen atom of an imino group may be substituted by an alkyl group, or a 6-membered heteroaromatic ring linked via a carbon atom, which contains 1 or 2 nitrogen atoms, whilst the phenyl group may additionally be substituted, as may the 5- and 6-membered heteroaromatic rings in their carbon skeleton, by a fluorine, chlorine or bromine atom, by an alkyl group, by a cycloalkyl group with 3 to 6 carbon atoms, by a phenylalkyl, alkoxy, trifluoromethyl, hydroxy or amino group, $R^2$ denotes a hydrogen atom, an alkyl group or a phenylalkyl group optionally substituted in the phenyl moiety by a fluorine, chlorine or bromine atom or by an alkyl, trifluoromethyl, amino or acetylamino group, $R^3$ denotes a hydrogen atom or the methyl group, Y denotes an oxygen atom or the -$NR^4$-group wherein $R^4$ denotes a hydrogen atom, the methyl or ethyl group, m denotes the number 1 and V, which is bound in the 4 position of the benzene ring, denotes a hydrogen, fluorine, chlorine or bromine atom, a cyano, alkyl, hydroxy, alkoxy, phenylalkoxy, alkylcarbonyl, dialkylamino, hydroxymethyl, hydroxyethyl, hydroxypropyl, hydroxybutyl or trifluoromethyl group or the group —$(CH_2)_o$—$Y^1$—$(CO)$—$Y^2$ wherein o denotes the number 0 or 1, $Y^1$ denotes a single bond, an oxygen atom or the group —$NR^5$, wherein $R^5$ denotes a hydrogen atom or a straight-chained or branched alkyl group with 1 to 4 carbon atoms or $R^5$ together with the group $Y^2$, the enclosed nitrogen atom and the enclosed group >C=O forms a saturated heterocyclic ring with 5 to 7 ring members, and $Y^2$ denotes a straight-chained or branched alkyl group with 1 to 5 carbon atoms optionally substituted by a hydroxy, alkoxycarbonyl or aminocarbonyl group, an alkoxy group with 1 to 3 carbon atoms, an aminoalkyl, alkylaminoalkyl or dialkylaminoalkyl group or a phenyl or phenylalkyl group with 1 to 3 carbon atoms in the alkyl moiety optionally substituted in the phenyl moiety by a fluorine, chlorine or bromine atom, by a methyl, trifluoromethyl, cyano, amino, hydroxy or methoxy group or the —$NR^6R^7$ group wherein $R^6$ denotes a hydrogen atom, a straight-chained or branched alkyl group with 1 to 6 carbon atoms, a cycloalkyl group with 4 to 6 carbon atoms or a phenyl group optionally substituted by a fluorine, chlorine or bromine atom, by a methyl, trifluoromethyl, hydroxy or methoxy group, and $R^7$ has the meanings given for $R^6$ with the exception of a phenyl group, whilst all the abovementioned alkyl, alkoxy, phenylalkyl, ω,ω-diphenylalkyl, naphthylalkyl, cycloalkylalkyl, phenylalkoxy, phenylalkoxycarbonyl, alkoxycarbonylalkyl, alkoxycarbonylmethoxy, carboxyalkyl, alkylamino, dialkylamino, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties, or a tautomer, diastereomer, enantiomer or physiologically acceptable salt thereof.

4. A compound of the formula Ia according to claim 2 wherein

R denotes a diphenylmethyl group wherein the phenyl groups independently of one another may be substituted by a methyl group, n denotes the number 0, U denotes a single bond, $R^1$ denotes a hydrogen atom, a straight-chained or branched alkyl group with 1 to 3 carbon atoms which may be terminally substituted by a cycloalkyl group with 4 to 6 carbon atoms, whilst the cycloalkyl group may in turn be substituted by a dialkylaminomethyl group with 1 to 3 carbon atoms in the alkyl moieties, the aminocarbonyl group, which may be substituted at the nitrogen atom by an alkyl group with 1 to 3 carbon atoms, or a phenyl group optionally substituted by an alkyl or alkoxy group with 1 to 3 carbon atoms, $R^2$ denotes a hydrogen atom or an alkyl group with 1 to 3 carbon atoms optionally substituted by a phenyl group, R³ denotes a hydrogen atom or the methyl group, Y denotes the —NR⁴ group wherein
R⁴ denotes a hydrogen atom, the methyl or ethyl group, m denotes the number 1 and V, which is bound in the 4 position of the benzene ring, denotes a hydrogen atom, a hydroxy or phenylalkoxy group with 1 to 3 carbon atoms in the alkoxy moiety or the group —CH₂—Y¹—(CO)—Y² wherein
Y¹ denotes a single bond or the group —NR⁵, wherein
R⁵ denotes a hydrogen atom or a straight-chained or branched alkyl group with 1 to 3 carbon atoms, and
Y² denotes the —NR⁶R⁷ group wherein
R⁶ and R⁷ independently of one another denote a hydrogen atom or a straight-chained or branched alkyl group having 1 to 3 carbon atoms, or a tautomer, diastereomer, enantiomer or physiologically acceptable salt thereof.

5. A compound selected from the group consisting of:

(1) (R,S)-3-(Aminoiminomethylamino)-α-[(diphenylacetyl)-amino]-N-[(4-hydroxyphenyl)methyl]-benzeneacetamide, (2) (R,S)-N-[[4-(Aminocarbonylaminomethyl)phenyl]methyl]-3-(aminoiminomethylamino)-α-[(diphenylacetyl)amino]benzeneacetamide, (3) (R,S)-N-[[4-(Aminocarbonylmethyl)phenyl]methyl]-3-(aminoiminomethylamino)-α-[(diphenylacetyl)amino]-benzeneacetamide, (4) trans-(R,S)-3-[[4-(Dimethylaminomethyl)cyclohexylmethyl]-aminoiminomethylamino]-α-[(diphenylacetyl)amino]-N-methyl-N-(phenylmethyl)benzeneacetamide, (5) (R,S)-α-[(Diphenylacetyl)amino]-N-methyl-3-(phenylaminoiminomethylamino)-N-(phenylmethyl)benzeneacetamide, (6) (R,S)-3-(Aminoiminomethylamino)-α-[(diphenylacetyl)amino]-N-methyl-N-(phenylmethyl)-benzeneacetamide, (7) (R,S)-α-[(Diphenylacetyl)amino]-N-methyl-3-(methylaminoiminomethylamino)-N-(phenylmethyl)benzeneacetamide, (8) trans-(R,S)-N-[[4-(Aminocarbonylaminomethyl)phenyl]methyl]-3-[[4-(dimethylaminomethyl)cyclohexylmethyl]aminoiminomethylamino]-α-[(diphenylacetyl)amino]-benzeneacetamide, (9) (R,S)-N-[[4-(Aminocarbonylaminomethyl)phenyl]methyl]-α-[(diphenylacetyl)amino]-3-[(methylaminocarbonyl)aminoiminomethylamino]-benzeneacetamide,

(10) (R,S)-N-[[4-(Aminocarbonylaminomethyl)phenyl]methyl]-α-[(diphenylacetyl)amino]-3-[(4-methoxyphenyl)aminoiminomethylamino]-benzeneacetamide,

(11) (R,S)-α-[(Diphenylacetyl)amino]-3-[(4-methoxyphenyl)aminoiminomethylamino]-N-(phenylmethyl)benzeneacetamide,

(12) (R,S)-N-[[4-(Aminocarbonylaminomethyl)phenyl]methyl]-α-[(diphenylacetyl)amino]-3-[[imino[N-methyl-N-(phenylmethyl)amino]methyl]amino]-benzeneacetamide,

(13) (R,S)-N-[[4-(Aminocarbonylaminomethyl)phenyl]methyl]-α-[(diphenylacetyl)amino]-3-(methylaminoiminomethylamino)-benzeneacetamide,

(14) (R,S)-α-[(Diphenylacetyl)amino]-3-[(4-methoxyphenyl)aminoiminomethylamino]-N-[[(4-phenylmethoxy)phenyl]-methyl]-benzeneacetamide,

(15) (R,S)-3-(Aminoiminomethylamino)-α-[(diphenylacetyl)amino]-N-[[(4-phenylmethoxy)phenyl]methyl]benzeneacetamide,

(16) (R,S)-3-(Aminoiminomethylamino)-α-[(diphenylacetyl)amino]-N-methyl-N-[[(4-phenylmethoxy)phenyl]methyl]benzeneacetamide,

(17) (R,S)-N-[[4-(Aminocarbonylaminomethyl)phenyl]methyl]-α-[(diphenylacetyl)amino]-N-methyl-3-(methylaminoiminomethylamino)-benzeneacetamide and a physiologically acceptable salt thereof.

6. A pharmaceutical composition comprising as an active substance a compound according to claims 1, 2, 3, 4 or 5 together with one or more inert carriers and/or diluents.

7. A method of treating a disease condition selected from the group consisting of hypertension, cardiovascular disease, coronary heart disease, subarachnoid bleeding, vascular hypertrophic changes, cerebral and coronary vasospasms, chronic kidney failure, tumoral disease, hyperthyroidism, obesity and diabetes which method comprises administering a effective therapeutically amount of a compound according to claim 1, 2, 3, 4 or 5.

8. A method of treating hypertension comprising administering a therapeutically effective amount of a compound according to claim 1, 2, 3, 4 or 5.

* * * * *